US011594315B2

(12) United States Patent
Oh et al.

(10) Patent No.: US 11,594,315 B2
(45) Date of Patent: Feb. 28, 2023

(54) SYSTEMS AND METHODS FOR AUTOMATIC ACTIVITY TRACKING

(71) Applicant: The Regents of the University of California, Oakland, CA (US)

(72) Inventors: Hyungik Oh, Irvine, CA (US); Ramesh C. Jain, Irvine, CA (US); Laleh Jalali, San Jose, CA (US)

(73) Assignee: The Regents of the University of California, Oakland, CA (US)

( * ) Notice: Subject to any disclaimer, the term of this patent is extended or adjusted under 35 U.S.C. 154(b) by 261 days.

(21) Appl. No.: 16/758,841

(22) PCT Filed: Oct. 23, 2018

(86) PCT No.: PCT/US2018/057111
§ 371 (c)(1),
(2) Date: Apr. 23, 2020

(87) PCT Pub. No.: WO2019/084007
PCT Pub. Date: May 2, 2019

(65) Prior Publication Data
US 2021/0183493 A1    Jun. 17, 2021

Related U.S. Application Data

(60) Provisional application No. 62/575,739, filed on Oct. 23, 2017.

(51) Int. Cl.
*G16H 20/60* (2018.01)
*A61B 5/0205* (2006.01)
(Continued)

(52) U.S. Cl.
CPC .......... *G16H 20/60* (2018.01); *A61B 5/0205* (2013.01); *A61B 5/1118* (2013.01); *A61B 5/7267* (2013.01)

(58) Field of Classification Search
CPC ......... G16H 20/60; G16H 40/20; G16H 50/30
See application file for complete search history.

(56) References Cited

U.S. PATENT DOCUMENTS

| 7,203,635 B2 | 4/2007 | Oliver et al. |
| 2011/0276396 A1 | 11/2011 | Rathod |
| 2017/0220772 A1* | 8/2017 | Vleugels ................ G16H 50/70 |

FOREIGN PATENT DOCUMENTS

| EP | 3064130 A1 | 9/2016 | |
| WO | WO-2008157622 A1 * | 12/2008 | ........... A61B 5/0022 |
| WO | 2019084007 A1 | 5/2019 | |

OTHER PUBLICATIONS

Vu, Tri, et al. "Wearable food intake monitoring technologies: A comprehensive review." Computers 6.1 (2017): 4. (Year: 2017).*

(Continued)

*Primary Examiner* — Linh Giang Le
*Assistant Examiner* — Constantine Siozopoulos
(74) *Attorney, Agent, or Firm* — KPPB LLP

(57) ABSTRACT

Systems and methods for tracking activities from a plurality of multimodal inputs are described. Activity tracking can include receiving a plurality of multimodal inputs, synchronizing the plurality of multimodal inputs, generating segments from the synchronized multimodal inputs, recognizing activities associated with each generated segment by performing a bagged formal concept analysis (BFCA), and recording the recognized activities in a storage. Tracking of activities can include the detection of moments (e.g., eating moments), during which an activity tracking application can prompt a user for information (e.g., a food journal).

20 Claims, 8 Drawing Sheets

(51) Int. Cl.
A61B 5/11 (2006.01)
A61B 5/00 (2006.01)

(56) References Cited

OTHER PUBLICATIONS https://www.google.com/fit [n. d.] Google Fit ([n. d.)].
International Preliminary Report on Patentability for International Application PCT/US2018/057111, Report Issued Apr. 28, 2020, dated May 7, 2020, 4 pgs.
International Search Report and Written Opinion for International Application No. PCT/US2018/057111, Search completed Dec. 10, 2018, dated Dec. 27, 2018, 9 pgs.
Abowd et al., "Towards a Better Understanding of Context and Context-Awareness", HUC '99: Proceedings of the 1st international symposium on Handheld and Ubiquitous Computing, Jan. 1999, pp. 304-307.
Albatal et al., "Senseseer mobile-cloud-based Lifelogging framework", 2013 IEEE International Symposium on Conference: Technology and Society (ISTAS), Jun. 2013, pp. 145-146, DOI: 10.1109/ISTAS.2013.6613113.
Bao et al., "Activity Recognition from User-Annotated Acceleration Data", Pervasive Computing, 2004, pp. 1-17.
Bell et al., "Total Recall: How the e-memory revolution will change everything", Dutton: New York, 2009. 19 pgs.
Biegel et al., "A Framework for Developing Mobile, Context-aware Applications", in Proceedings of the Second IEEE Annual Conference on Pervasive Computing and Communications, 2004, pp. 361-365.
Bush, "As we may think", The Atlantic Monthly, 1945, No. 176, No. 1, pp. 112-124.
Carter et al., "Momento: Support for situated ubicomp experimentation", Proceedings of the 2007 Conference on Human Factors in Computing Systems, Jan. 2007, CHI 2007, San Jose, California, USA, Apr. 28-May 3, 2007, pp. 125-134, DOI: 10.1145/1240624.1240644.
Ceravolo et al., "Extending Formal Concept Analysis by Fuzzy Bags", IPMU; Publication 2006, pp. 1-9.
Chen et al., "A Knowledge-Driven Approach to Activity Recognition in Smart Homes", IEEE Transactions on Knowledge and Data Engineering, Jun. 2012, vol. 24, Issue: 6, pp. 961-974, DOI: 10.1109/TKDE.2011.51.
Choe et al., "Semi-Automated Tracking: A Balanced Approach for Self-Monitoring Applications", IEEE Pervasive Computing, Jan.-Mar. 2017, vol. 16, No. 1, pp. 74-84.
Dey, "Understanding and Using Context", Personal and Ubiquitous Computing, Feb. 2001, vol. 5, pp. 4-7, DOI: 10.1007/s007790170019.
Doherty et al., "Automatically segmenting lifelog data into events", IEEE 2008 Ninth International Workshop on Image Analysis for Multimedia Interactive Services, May 7, 2008, 4 pgs.
Ferreira et al., "Aware: mobile context instrumentation framework", Frontiers in ICT, Apr. 20, 2015, vol. 2, Article 6, pp. 1-9, https://doi.org/10.3389/fict.2015.00006.
Fogarty et al., "Sensing from the basement: a feasibility study of unobtrusive and low-cost home activity recognition", UIST '06: Proceedings of the 19th Annual ACM Symposium on User Interface Software and Technology, Oct. 2006. pp. 91-100, https://doi.org/10.1145/1166253.1166269.
Fontana et al., "Detection and Characterization of Food Intake by Wearable Sensors", Wearable Sensors, Fundamentals, Implementation and Applications, 2014, pp. 591-616, https://doi.org/10.1016/B978-0-12-418662-0.00010-6.
Gemmell et al., "MyLifeBits: a personal database for everything", Communications of the ACM, Jan. 2006, vol. 49, No. 1, pp. 89-95, DOI: 10.1145/1107458.1107460.
Gemmell et al., "MyLifeBits: Fulfilling the Memex Vision", Memex Vision, Proceedings of the ACM International Multimedia Conference and Exhibition, Jul. 2002, pp. 235-238, DOI: 10.1145/641007.641053.
Gurrin et al., "LifeLogging: Personal Big Data", Foundations and Trends in Information Retrieval, 2014, vol. 9, No. 1, pp. 1-107, DOI: 10.1561/1500000033.
Hong et al., "Toward Personalized Activity Recognition Systems With a Semipopulation Approach", IEEE Transactions on Human-Machine Systems, Nov. 2015, pp. 101-112, DOI: 10.1109/THMS.2015.2489688.
Intelle et al., "Just-in-Time Context-Sensitive Questioning for Preventative Health Care", AAAI 2002 Workshop on Automation as Caregiver: The Role of Intelligent Technology in Elder Care, Technical Report WS-02-02, 6 pgs.
Jain et al., "Objective self", IEEE MultiMedia, Oct.-Dec. 2014, vol. 21, No. 4, pp. 100-110.
Jalali et al., "Human Behavior Analysis from Smartphone Data Streams", International Workshop on Human Behavior Understanding, Lecture Notes in Computer Science, Oct. 2016, pp. 68-85, DOI: 10.1007/978-3-319-46843-3_5.
Jalali et al., "Personicle: Personal Chronicle of Life Events", in Workshop on Personal Data Analytics in the Internet of Things (PDS@IOT) at the 40th International Conference on Very Large Databases (VLDB), Jul. 2014, 9 pgs.
Kahneman et al., "A survey method for characterizing daily life experience: the day reconstruction method", Science, Dec. 3, 2004, vol. 306, No. 5702, pp. 1776-1780, doi: 10.1126/science.1103572.
Korpusik, "Spoken Language Understanding in a Nutrition Dialogue System", Thesis, Jun. 2015, 111 pgs.
Korpusik et al., "Data Collection and Language Understanding of Food Descriptions", IEEE, SLT 2014, pp. 560-565.
Korpuski et al., "Convolutional Neural Networks and Multitask Strategies for Semantic Mapping of Natural Language Input to a Structured Database", ICASSP 2018, Apr. 12, 2018, pp. 6174-6178.
Kwapisz et al., "Activity Recognition using Cell Phone Accelerometers", ACM SIGKDD Explorations Newsletter, vol. 12, No. 2, Dec. 2010, pp. 74-82.
Lin et al., "Experiencing SAX: a novel symbolic representation of time series", Data Mining and Knowledge Discovery, Apr. 3, 2007, vol. 15, pp. 107-144, DOI: 10.1007/s10618-007-0064-z.
Lustrek et al., "Recognising lifestyle activities of diabetic patients with a smartphone", EAI Endorsed Transactions on Pervasive Health and Technology, May 2015, vol. 1, No. 4, pp. 317-324, DOI: 10.4108/icst.pervasivehealth.2015.259118.
Merck et al., "Multimodality Sensing for Eating Recognition", 10th EAI International Conference on Pervasive Computing Technologies for Healthcare, Jun. 6, 2016, 8 pgs., doi: 10.475/123_4.
Mittal et al., "A versatile lattice based model for situation recognition from dynamic ambient sensors", International Journal on Smart Sensing and Intelligent Systems, Feb. 2013, vol. 9, No. 6, pp. 403-432, DOI: 10.21307/ijssis-2017-547.
Naphtal, "Natural Language Processing Based Nutritional Application", Thesis, Jun. 2015, 68 pgs.
Oh et al., "A Life Event Detection System Using Real-Time Heterogeneous Context Monitoring 1-20 and Formal Concept Analysis", UC Irvine Electronic Thesis and Dissertations; Publication 2015; pp. 1-63.
Oh et al., "An intelligent notification system using context from real-time personal activity monitoring", Conference: The IEEE International Conference on Multimedia & Expo, Jul. 2015, pp. 1-6, DOI: 10.1109/ICME.2015.7177508.
Rahman et al., "Predicting "About to Eat" Moments for Just-in-Time Eating Intervention", Proceedings of the 6th International Conference on Digital Health Conference, Apr. 2016, pp. 141-150, https://doi.org/10.1145/2896338.2896359.
Sazonov et al., "A Sensor System for Automatic Detection of Food Intake Through Non-Invasive Monitoring of Chewing", IEEE Sensors Journal, May 2012, vol. 12, Issue: 5, first published Oct. 7, 2011, DOI: 10.1109/JSEN.2011.2172411, pp. 1340-1348.
Sellen et al., "Beyond Total Capture: A Constructive Critique of Lifelogging", Communications of the ACM, May 2010, vol. 53, No. 5, DOI: 10.1145/1735223.1735243, pp. 70-77.
Tapia et al., "Activity Recognition in the Home Using Simple and Ubiquitous Sensors", Pervasive Computing, LNCS 3001, 2004, pp. 158-175.

(56) References Cited

OTHER PUBLICATIONS

Van Kasteren et al., "Accurate activity recognition in a home setting", Ubiquitous Computing, 10th International Conference, Jan. 2008, DOI: 10.1145/1409635.1409637, 9 pgs.

Vu et al., "Wearable Food Intake Monitoring Techniques: A Comprehensive Review", Computers, Jan. 24, 2017, vol. 6, No. 4, pp. 1-28, doi:10.3390/computers6010004.

Wang et al., "Characterizing Everyday Activities from Visual Lifelogs based on Enhancing Concept Representation", Computer Vision and Image Understanding, vol. 148, Jun. 22, 2016, pp. 181-192.

Wang et al., "Enhancing the Detection of Concepts for Visual Lifelogs Using Contexts Instead of Ontologies", IEEE International Conference on Multimedia and Expo Workshops (ICMEW), Sep. 2014, DOI: 10.1109/ICMEW.2014.6890570, 6 pgs.

Wang et al., "Semantics-Based Selection of Everyday Concepts in VisualLifelogging", International Journal of Multimedia Information Retrieval, Mar. 16, 2012, vol. 1, pp. 87-101, DOI: 10.1007/s13735-012-0010-8.

Westermann et al., "Toward a Common Event Model for Multimedia Applications", IEEE Computer Society, Jan.-Mar. 2007, vol. 14, No. 1, pp. 19-29, DOI: 10.1109/MMUL.2007.23.

Yang, "Toward Physical Activity Diary: Motion Recognition Using Simple Acceleration Features with Mobile Phones", Proceedings of the 1st International Workshop on Interactive Multimedia for Consumer Electronics, Jan. 2009, pp. 1-10, DOI: 10.1145/1631040.1631042.

FitBit, https://www.fitbit.com/home, Retrieved from Wayback Machine on Sep. 15, 2017, 4 pgs.

"Chronicle", Artefact Group, https://www.artefactgroup.com/case-studies/chronicle/, Retrieved from Wayback Machine on Oct. 1, 2020, 10 pgs.

Cao et al., "GCHAR: An efficient Group-based Context—aware human activity recognition on smartphone", Journal of Parallel and Distributed Computing, vol. 118, Part 1, Aug. 2018, pp. 67-80.

Diaz-Rodriguez et al., "Handling Real-World Context Awareness, Uncertainty and Vagueness in Real-Time Human Activity Tracking and Recognition with a Fuzzy Ontology-Based Hybrid Method", Sensors (Basel), vol. 14, No. 10, Oct. 2014, pp. 18131-18171.

Intille et al., "Using a Live-in Laboratory for Ubiquitous Computing Research", Part of the Lecture Notes in Computer Science book series, vol. 3968, International Conference on Pervasive Computing, Dublin, Ireland, May 7-10, 2006, pp. 349-365.

Oh et al., "Multimodal Food Journaling", HealthMedia'18: Proceedings of the 3rd International Workshop on Multimedia for Personal Health and Health Care, Oct. 2018, pp. 39-47.

Sbeyti et al., "Scalable extensible middleware framework for context-aware mobile applications (SCAMMP)", Journal of Wireless Mobile Networks, Ubiquitous Computing, and Dependable Applications, vol. 7, No. 3, Sep. 2016, pp. 77-98.

Yurur et al., "Energy-Efficient and Context-Aware Smartphone Sensor Employment", IEEE Transactions on Vehicular Technology, vol. 64, No. 9, Sep. 2015, pp. 4230-4244.

\* cited by examiner

SYSTEMS AND METHODS FOR AUTOMATIC ACTIVITY TRACKING

CROSS-REFERENCE TO RELATED APPLICATIONS

This application is a U.S. national phase of PCT Application No. PCT/US2018/057111 filed on Oct. 23, 2018, which claims the benefit of U.S. Provisional Patent Application No. 62/575,739 filed on Oct. 23, 2017, the disclosures of which are incorporated in their entirety by reference herein.

FIELD OF THE INVENTION

The present invention generally relates to activity tracking and more specifically relates to novel and inventive methods for automatic activity tracking from multimodal inputs and the characterization of activities.

BACKGROUND

Understanding the daily lives of human beings, what people have experienced, how people have spent their time, when and where they have been and whom they have been with, has long been the subject of scientific inquiry. This interest has led people in the field of multimedia to develop scientific approaches to monitoring and analyzing personal lifestyles and behavioral patterns. Significant advances in computer storage, processing power, sensing technology, and network systems have encouraged researchers to participate in the field of human behavior recognition, using a variety of techniques. In some cases, researchers use activity trackers, which are devices or applications for monitoring and tracking metrics such as distance traveled and calorie consumption. Multimedia researchers have tried to extract semantic level information from visual content so that they can analyze people's lives, and even environmental conditions and social situations. They also have analyzed real-time behavior data, which is collected via wearable devices, such as smartphones or smartbands, and social media, to understand more about personal lifestyles and behavioral patterns. The tracking of different activities can also include tracking specific details of an activity. For example, tracking an individual's food consumption can be used for various medical and health objectives. A food journal can be essential for improving health and well-being. However, journaling every meal can be difficult because it depends on user initiative and intervention. Current approaches to food journaling are both potentially inaccurate and tedious, causing people to abandon their journals very soon after they start.

SUMMARY OF THE INVENTION

Systems and methods for tracking activities from a plurality of mulimodal inputs in accordance with embodiments of the invention are described. One embodiment includes a method that receives a plurality of multimodal inputs, synchronizes the plurality of multimodal inputs, generates segments from the synchronized multimodal inputs, recognizes activities associated with each generated segment by performing a bagged formal concept analysis (BFCA), and records the recognized activities in a storage.

In another embodiment, performing the BFCA comprises creating a plurality of classifiers, selecting a random subset of attributes for each classifier of the plurality of classifiers, training the plurality of classifiers based on the associated selected random subsets of attributes, generating a new model for labeling new input attribute sets based on the trained plurality of classifiers, and generating a label for a new attribute set using the new generated model.

In a further embodiment, the generated new model comprises at least one of a cross table and a concept lattice.

In still another embodiment, the plurality of multimodal inputs comprises at least one of data from applications operating on a mobile phone and data from a set of one or more sensors.

In a still further embodiment, synchronizing the plurality of multimodal inputs comprises associating data from the multimodal inputs from a given time period with a plurality of atomic intervals, wherein each atomic interval has a same duration.

In yet another embodiment, generating segments from the synchronized multimodal inputs comprises performing a binary interval growing operation.

In a yet further embodiment, performing a binary interval growing operation comprises identifying an initial atomic interval for a particular segment. For a second atomic interval, a transition moment is identified, and each atomic interval from the initial atomic interval to the second atomic interval is identified as a single segment.

In another additional embodiment, the transition moment comprises a change between a non-moving state and a moving state.

In a further additional embodiment, the method further comprises determining whether to retrieve supplemental data upon detecting a trigger event, and, upon determining that the trigger event has been detected, retrieving the supplemental data.

In another embodiment again, the trigger event is recognition of an eating moment and retrieving the supplemental data comprises providing an audio prompt to record a food journal entry.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

DETAILED DESCRIPTION

Figure 1A:
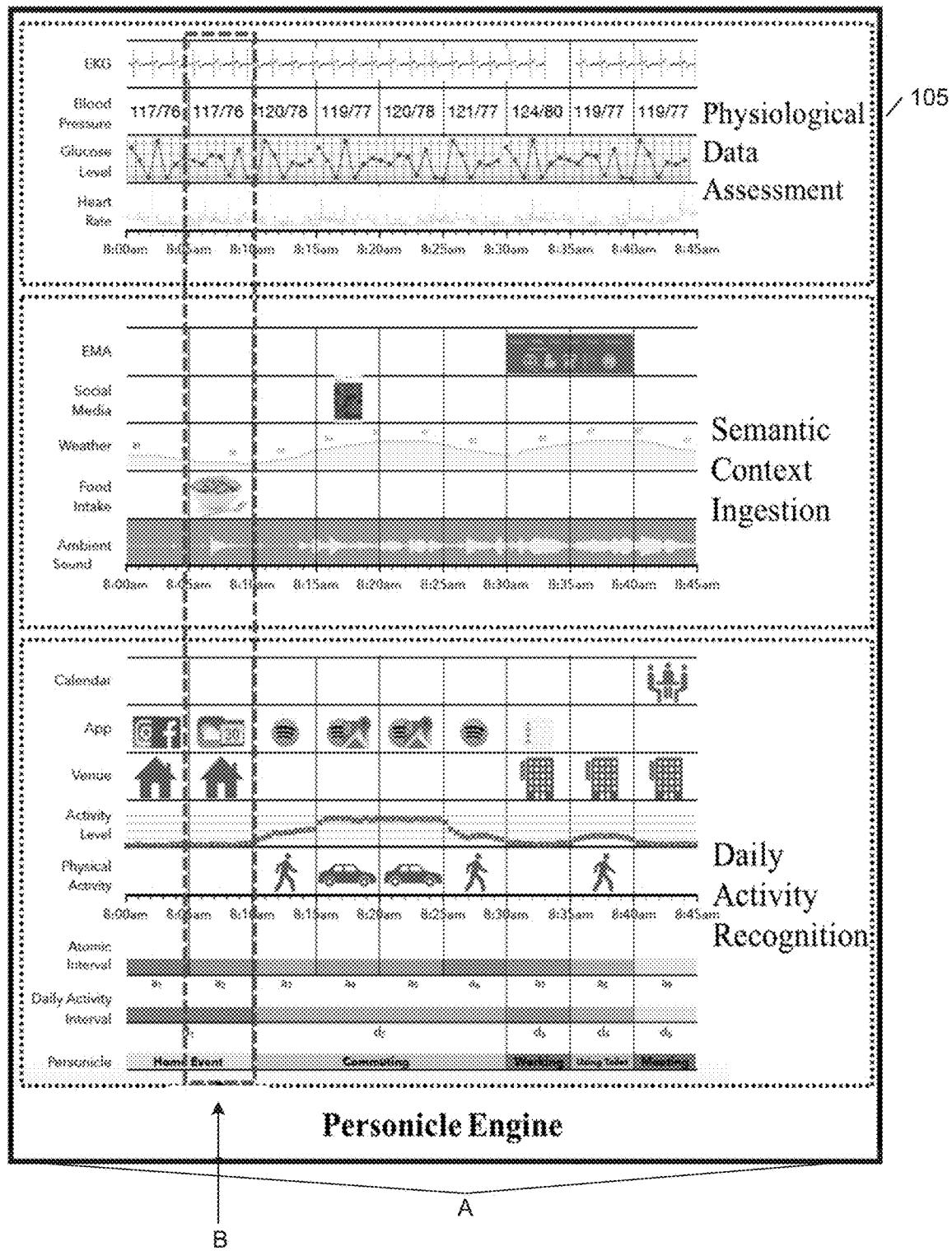
FIG. 1 illustrates a conceptual example of mutimodal data streams in accordance with an embodiment of the invention.

Turning now to the drawings, systems and methods for automatic activity tracking in accordance with embodiments of the invention are disclosed. Although many of the examples described below are described with reference to activity tracking applications, one skilled in the art will recognize that systems and processes in accordance with various embodiments of the invention can be applied to other types of analyses for time-aligned, multimodal input data streams. Personalized daily chronicles, which present organized breakdowns of a persons daily activities, can shed significant insight into an individuals health and behavior, and may even provide early indicators of physical or mental health disorders. Recent advances in user devices (such as, but not limited to, smartphones, and wearable devices) incorporate many advanced built-in sensors (e.g., cameras, microphones, accelerometers, gyroscopes, heartrate trackers, location trackers, etc.) and have opened new possibilities for continuous, unobtrusive monitoring of a persons activities (context awareness). However, currently, unobtrusively collecting and integrating data collected from a users devices, subsequently translating this data into meaningful personal daily activities, and recognizing people's daily lives at higher cognitive and more abstract levels (e.g., working, exercising, shopping, or relaxing) rather than low-level multimedia lifelogs (e.g., step count, GPS, venue, or physical activity) remains relatively undeveloped. Applications that track an individuals activity in accordance with a number of embodiments of the invention can harness the data collected from these existing applications to detect and identify a user's activities. Activities can include (but are not limited to) walking, driving, social media use, texting, etc.

As these multimodal data streams (or lifelogs) are collected within different applications and over different time frames, they can have varying granularities (levels of detail) and semantics (imparted interpretation). However, to truly understand a persons activities, these events must often be interpreted into higher-order and more meaningful daily activities, which include more specialized classifications such as (but not limited to) commuting to work, working, exercising, relaxing, etc. In order to construct a useful personal chronicle, these data streams must first be synchronized within one central application from which they can then be analyzed simultaneously. The synchronized data streams can then be raised up to higher-level forms, so-called daily activity, by analyzing relationships between the daily activity and their temporal, causal, spatial, experiential, informational, and structural aspects. Finally, the personal chronicle of the daily activity can be generated by chronologically ordering the recognized results.

Activity tracking systems in accordance with embodiments of the invention overcome the limitations of existing activity tracking systems by automatically characterizing a users daily activities to provide a useful personal chronicle. Automatic activity tracking systems can correlate diverse data streams and define atomic-intervals by constantly recording data collected from a variety of sensors to track user activity. These atomic-level activities can be collected as diverse data streams that are correlated in the application using periodic time intervals (atomic-intervals). Each atomic-interval may contain one or more distinct atomic-level activities, depending on the users activity within that time frame. Atomic-level activities (i.e. walking, standing still, making a phone call, etc.) can be read immediately from a user's device usage without any initial interpretation over a variety of timeframes, while higher-level activities can be identified based on a combination of synchronized events over a period of time. In many embodiments, five minutes serves as an appropriate time frame, which segments a users day into 288 atomic-intervals. Each atomic interval can then be organized by the activity level, type, venue, and application from which the event was collected.

The atomic-intervals can be translated into daily-activity-intervals, via an interval growing technique (IGT) in accordance with a number of embodiments of the invention. In many embodiments, IGT can analyze sequential atomic-level intervals and group similar intervals together to make a daily-activity-interval. For example, several sequential atomic-intervals consisting of walking can be grouped together into a single, longer daily-activity-interval. Any changes in physical activity can be read as a change in daily activity. For example, if a user gets up from his desk at work after a long period of sitting, the change from still to walking is used to identify the end of one activity and start of another. In certain embodiments, a change between a "moving" state and a "non-moving" state is used to signal an end to an interval.

Daily-activity-intervals in accordance with certain embodiments of the invention can be labeled as daily activities using Bagging Formal Concept Analysis (BFCA). This can include taking segmented groups of daily activities, such as walking or still, and identifying their higher order meanings, such as walking to work or working. Similar technologies have used Formal Concept Analysis (FCA), a hierarchal grouping technique that organizes objects based on their attributes and interrelationships. From this, FCA interprets that a walking event for a short time duration while at work corresponds to using the toilet while a medium time duration corresponds with commuting. However, standard FCA has no embedded statistical analysis and depends only on the structural similarity between objects without taking into account the various probabilities of each event. For example, a user whose phone records still at home for eight hours straight (i.e. 12 am 8 am) is likely sleeping, though standard FCA may also assign other activities such as eating or relaxing as it has no way of weighting these activities by their respective probabilities. To combat this ambiguity, BFCA can be utilized. BFCA applies an ensemble approach to FCA, whereby activity classifications are weighted by their likelihood of occurring, based on previously collected trends and typical activity attributes. For example, activities such as sleep and work comprise the majority of a users day, and so are weighted more heavily than activities such as eating.

In many embodiments, intervals can be labeled based on the detection of particular activities. For example, processes in accordance with a number of embodiments of the invention can detect that a user has begun an eating activity. Detecting that a user has begun eating in accordance with some embodiments of the invention can be performed based on sensors from one or more devices of a user. For example, in some embodiments, an eating activity is detected based on a user's heartrate measured from a first device and a user's position and activity level measured from a second device. In certain embodiments, the detection of an activity can be used to trigger additional events, such as (but not limited to)

notifications, requests for data (e.g., a prompt for what a user is eating), and the recording of environmental data (e.g., heartrate, temperature, ambient noise, light levels, etc.).

Based on the labeled activity data, sets of daily activities can be compiled into a personal chronicle in accordance with some embodiments of the invention outlining a users events and their durations. From these chronicles, users can see an organized breakdown of their day, and keep track of things like work productivity, physical activity, and social interactions in a given day. Additionally, comparing these trends over time can serve as a useful indicator of changes to health, such as the onset of depression (indicated by increased sleep and decreased social interactions and productivity) or diabetes (indicated by more frequent trips to the bathroom). Personal chronicles in accordance with many embodiments of the invention can be used to model the activities of an individual. Modeling an individual can help them with personalized health management and objectively understanding the daily activities of human beings has a strong potential to improve health research, given that these daily activities and the sequences of these high-level data abstractions contain their life experiences, lifestyle, behavioral patterns, and even their feelings.

In many embodiments, data streams (or lifelogs) are collected automatically from all sensors and applications in a user's device(s) without any user intervention or action required. In several embodiments, activity tracking systems utilize standard smartphones, thereby requiring no additional equipment beyond a standard smartphone. In a variety of embodiments, data collection and interpretation happens entirely within devices that are nearly constantly with a user (such as, but not limited to, a smartphone, a smart watch, and other wearable smart devices) and so does not intervene with a users natural life patterns. This also prevents users from falsifying their activity reports.

Multimodal Data Streams

Multimodal data streams are essential for analyzing personal life, environmental conditions, and social situations. Since these data streams have different granularities and semantics, the semantic gap becomes even more formidable. Multimodal data streams in accordance with some embodiments of the invention can include streams from one or more devices (such as, but not limited to, a smartphone, a wearable device, and a cloud service). To make sense of all the multimodal correlated streams, processes in accordance with some embodiments of the invention synchronize the correlated streams in the context of an application, and then analyze them to extract meaningful information. Systems and methods in accordance with some embodiments of the invention can model an individual by using daily activity in order to understand their health and behavior. In many embodiments, diverse data streams are correlated with atomic-interval, and segment a person's day into his or her daily activities. Processes in accordance with a number of embodiments of the invention can collect diverse data streams from the person's smartphone to classify every atomic-interval into a daily activity. In certain embodiments, an interval growing technique can be used for determining daily-activity-intervals and their attributes. Daily-activity-intervals in accordance with several embodiments of the invention can be labeled as daily activities by using Bagging Formal Concept Analysis (BFCA). Finally, processes in accordance with some embodiments of the invention can build a personal chronicle, which is a person's time-ordered list of daily activities. Personal chronicles can then be used to model the person using learning techniques applied to daily activities in the chronicle and relating them to biomedical or behavioral signals.

In some embodiments, automatic recognition of activities from multimodal data streams can also be used to collect supplemental data for a recognized activity. Supplemental data can include (but is not limited to) a record of food that is eaten, a person's mood or mental state, and a description of bodily health. Such supplemental data can be used to build or supplement additional data sources that can be used to evaluate an individual, such as (but not limited to) a food journal and a record of a person's mood throughout a given time period.

Food journals can be essential for improving health and well-being. However, journaling every meal is extremely difficult because it depends on user initiative and intervention. Current approaches to food journaling are both potentially inaccurate and tedious, causing people to abandon their journals very soon after they start. Processes in accordance with many embodiments of the invention can provide proactive and reactive mechanisms that can significantly reduce user initiative while still remaining highly accurate. In some embodiments, a novel eating moment recognition technique uses heart rate and activity patterns to trigger a food journaling process in a proactive manner. Food journaling processes in accordance with a number of embodiments of the invention can then be triggered via voice commands, which can utilize natural language processing when logging meals. Voice commands can increase the ease of reactive self-reporting. In certain embodiments, food journals can be enhanced by automatically assessing ecological moments of eating activity through our personal chronicle system.

Figure 1B:
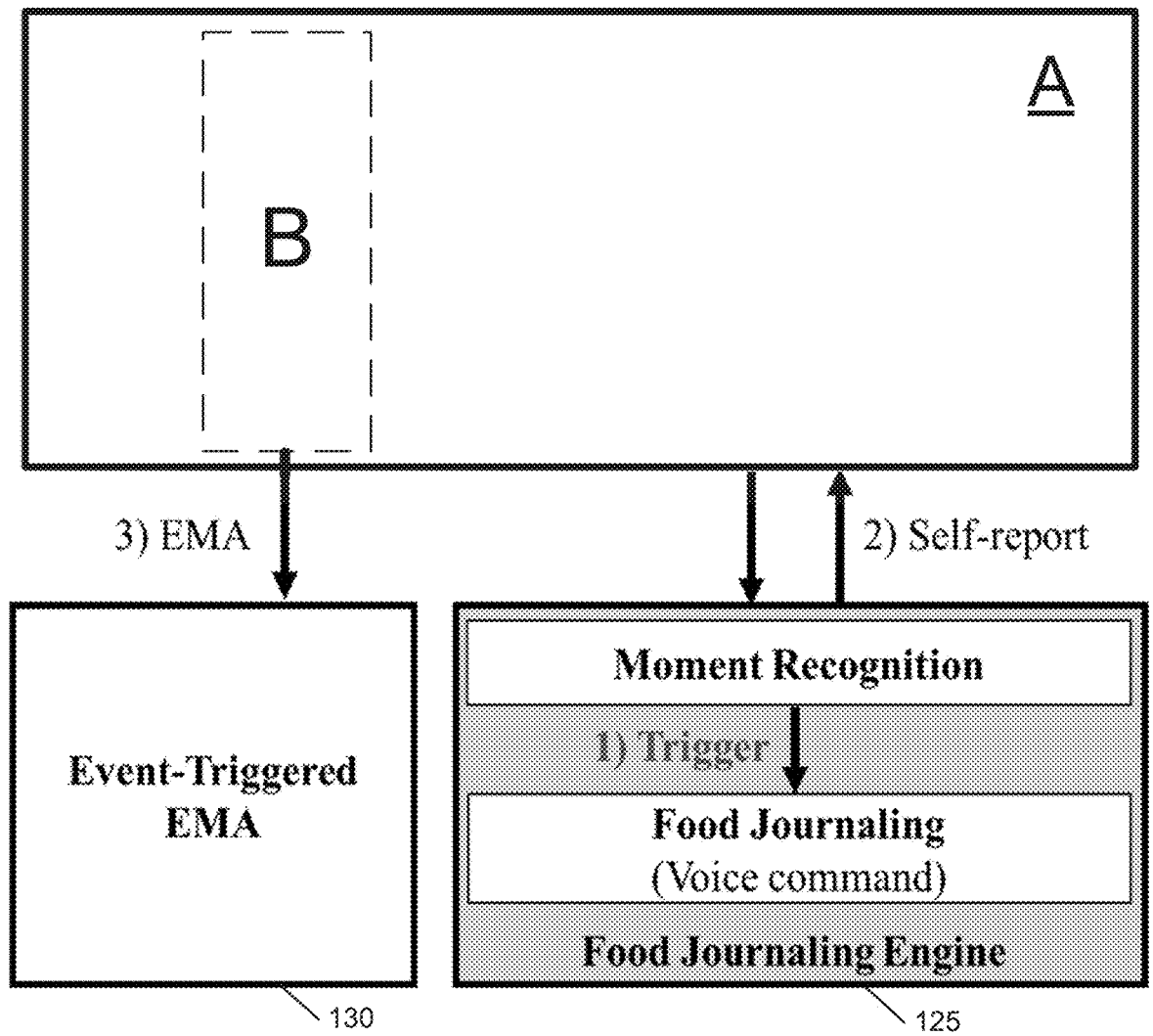

A conceptual example of multimodal data streams is illustrated in FIG. 1. In this figure, data streams 100 show a variety of different streams that can be captured by a set of one or more user devices. In this example, data streams include physiological data (e.g., EKG, blood pressure, heart rate, etc.), semantic context (e.g., social media, weather, ambient sound, etc.), and other daily activity data (e.g., calendar, location, active applications, activity levels, etc.). Data streams 105 are then synchronized with atomic interval segments 110 along a timeline. Atomic interval segments 110 are then segmented into daily activity intervals 115. Segmenting in accordance with some embodiments of the invention can be performed using an interval growing technique, as described herein. In numerous embodiments, activity intervals 115 are then identified (or labeled) and compiled into a personal chronicle 120. This example also shows a food journaling engine 125 and event-triggered EMA 130.

Food journaling engines in accordance with various embodiments of the invention can be a part of an activity tracker application or may operate as a separate application that interfaces with an activity tracker application. In various embodiments, food journaling engines can recognize moments (e.g., eating moments) and trigger an event, such as (but not limited to) a voice command prompt, a notification, and/or other methods for gathering supplemental data such as the contents of a meal.

Advances in sensor technology have increased the number of quantitative and qualitative multimedia lifelogs (or multimodal data streams) that are captured via a user's devices (e.g., wearables, smartphones, etc.). Heterogeneous multimedia streams can be automatically aggregated and analyzed in accordance with certain embodiments of the invention. Since multimodal data streams have different granularity and semantics, the data streams often need to be correlated by synchronizing them in the context of the application. In several embodiments, the synchronized data streams can then be raised up to higher-level forms, so-called daily activity, by analyzing relationships between the daily activity and their temporal, causal, spatial, experiential, informational, and structural aspects. Recognition approaches for identifying such higher-level forms can include collecting multimedia lifelogs, synchronizing and segmenting the data streams, recognizing daily activities, and generating the personal chronicle.

Modeling an individual (and their activity) can ultimately be used to help them with personalized health management. Objectively understanding the daily activities of human beings has a strong potential to improve health research, given that these daily activities and the sequences of these high-level data abstractions contain their life experiences, behavioral patterns, and even their feelings. According to Kahneman et al., quantifying information about time usage and its frequency, as well as stress level, pleasure, and other affective states of each individual user, can be useful for health research.

Analyzing personal chronicles of daily activities can be used to build sophisticated objective self models that can help the monitoring of individual health and building disease models. Objective self models are described in greater detail in the publication by Jain and Jalali, entitled "Objective Self", published in *IEEE MultiMedia* 21, 4 (2014), 100-110, the disclosure of which is incorporated by reference herein in its entirety.

To automatically quantify the daily activity of each individual, the recognition method should be unobtrusive and effortless, and user tracking should only use common devices. It is desirable to avoid intervening in users' life patterns by pushing them to do something or putting them in specific situations in order to recognize their daily activity. However, one major technical challenge is that this sort of fully-automated tracking is not always a guarantee of high recognition accuracy. Some daily activities might require more diverse features than current smartphone sensors, and some others might be user-dependent or subjective daily activities, which need user feedback for personalization. Processes in accordance with certain embodiments of the invention perform activity recognition and provide proactive and/or reactive prompts to gather timely and accurate information from a user with minimal interactions and effort.

In a variety of embodiments, processes can begin with understanding daily-activity-intervals by classifying every atomic-interval into a daily activity. Daily activities in a time-line are similar to objects in two-dimensional pixel space in that both the daily activities and objects are determined by a correlation between the times/pixels. Processes in accordance with several embodiments of the invention collect multimedia logs via each individual's device(s). Collected logs can be used to segment a person's day into their daily activities. Diverse data streams from a person's device(s) can be used to classify every atomic-interval into a daily activity. In a number of embodiments, interval growing techniques can be used to determine daily-activity-intervals and their attributes. In various embodiments, these daily-activity-intervals can then be labeled as the daily activities by using Bagging Formal Concept Analysis (BFCA). Daily activities in accordance with numerous embodiments of the invention can then be used to build a personal chronicle represented as events. Recognizing atomic-level daily activities, which can be automatically recognized, is one important step towards higher-level activity recognitions. Some of the benefits and improvements to current processes include 1) revealing and quantifying these atomic-level daily activities with our automated and unobtrusive approach, 2) increasing the possibility of automatically recognizing the higher cognitive daily activities, and 3) quantifying the personal chronicle of these daily activities.

Methodology Overview

In this section, an overall methodology for recognizing daily activity is described. First, daily activities are explained, and then the target corpus of the daily activity is finalized. Next, the daily activity corpus is categorized into three levels that describe their characteristics in terms of recognition possibility. Lastly, each daily activity is defined.

Daily activity is a brief name for each episode, such as "commuting to work" or "eating lunch", that can generally happen in the daily lives of human beings. Thus, the continuous series of the daily activities can imply the person's lifestyle, behavioral patterns, and even their feelings. Kahneman et al. have also insisted that quantifying these daily activities would potentially be useful for research on human well-being. Furthermore, they have tried to categorize common daily activities by conducting a survey, and suggested 16 common daily activities. In some embodiments, daily activities are refined into Kahneman's daily activity corpus, which has already been verified for human well-being research.

| Level 1 | Level 2 | Level 3 |
| --- | --- | --- |
| Still | Working | Watching TV |
| Walking | Commuting | Preparing food |
| Running | Exercising | Socializing |
| Cycling | Religions event | Housework |
| Driving | Shopping | Intimate relations |
| Direct communication | Eating | Relaxing |
| Remote communication | Using toilet | Taking a break |
| On the smartphone | Home event | Sleeping |

In the table above, Kahneman's common daily activities are classified in three levels. The level definitions are as follows:
Level 1 (L1): a daily activity which can be automatically recognized. It can be seen as the atomic-level.
Level 2 (L2): a daily activity which has the possibility of automatic recognition in the near future using sensing technology, but can not yet be recognized.
Level 3 (L3): a daily activity which is not possible to be automatically recognized, but is soon to be recognized once richer data is gathered. Subjective or user-dependent daily activities can also be deemed as level 3.

Since there are limits and restrictions on smartphone-based recognition, such as the lack of sensor data, or difficulties in understanding user-dependent or subjective activities, it may not be possible to recognize all the daily activities at the current stage. One approach is to focus on recognizing daily activities, which can be automatically recognized via smartphone first (atomic-level), and then gradually try to recognize the daily activities which have a high possibility of automatic recognition (L2). Once the daily activity is recognized, that activity can be considered the atomic-level activity, and it can be used as an attribute for other daily activity recognitions.

Kahneman's L2 activities can be defined based on their dictionary definitions. People might have different definitions for each daily activity. The following general definitions can be used for consistent labeling of daily activities:

Working: the activity of doing a job at the workplace (indoors).

Commuting: the activity of traveling regularly between work and home.

Exercising: the activity of performing physical actions to make or keep your body healthy.

Religious event: the activity occurring at religious places.

Shopping: the activity of looking for things to buy in a shopping mall.

Eating: the activity of taking food in a restaurant.

Using toilet: the activity of going to the bathroom.

Home event: the activity occurring in a structure in which a person lives, esp. a house or apartment.

Life Logging

Lifelogging signifies the process of gathering, processing, and storing data regarding personal life experiences. In several embodiments, processes can collect, process, and record a user's contextual information while the user is carrying their smartphone. As shown in FIG. 1, each exclusive data receiver, which is responsible for the generation of each data stream, can pull or process the collectable data independently using built-in smartphone sensors and different APIs in accordance with many embodiments of the invention. Agents can continually operate in the background of each user device, logging the data without any user interventions, and storing the derived results locally on the device for user-studies. Lifelogs can include (but are not limited to) the following:

- time: time_window (e.g., 20161028.59), time_band (e.g., 0: 00:00-03:59, 1: 04:00-07:59, 2: 08:00-11:59, 3: 12:00-15:59, 4: 16:00-19:59, 5: 20:00-23:59), week (e.g., 0: week, 1: weekend), long_time (e.g., 1477655468)
- location: latitude, longitude, venue_name (e.g., [Cheesecake Factory, Starbucks, Yogurt Land]), venue_type (e.g., [restaurant, cafe, food]), venue_likelihood (e.g., [30%, 10%, 5%]), point_of_interest
- activity: activity-type (e.g., [still, walking]), duration (e.g., [250, 50]), activity_level (e.g., 0.4012)
- phone oriented lifelog:
  1. application: count, name (e.g., [off, Facebook]), category (e.g., [none, communication]), duration (e.g., [200, 1001)
  2. photo: count, concept (e.g., (person, pasta, dish, man, woman])
  3. media: play time
  4. sound setting: silence, bell, vibration
  5. calendar: event (e.g., birthday party), where (e.g., Cheesecake Factory), start_time, end_time In some embodiments, processes can collect not only low-level lifelogs, such as latitude and longitude, but also high-level semantics. For example, processes in accordance with numerous embodiments of the invention provide a venue name set (e.g., [Cheesecake Factory, Starbucks, Yogurt Land]), which is the exact names of a given GPS point, and the categories of that venue (e.g., [restaurant, cafe, food]). Considering one GPS point may contain multiple venues, processes in accordance with a variety of embodiments of the invention can also provide the probabilities of being at each venue (e.g., [30%, 10%, 5%]). In several embodiments, processes can analyze the places the user frequently visited, and provide the user's point of interests. Processes in accordance with various embodiments of the invention can accumulate a sequence of the user's physical activity, calculate activity level, which is an average score of the physical activity set, and then provide these as high-level lifelogs.

| atomic interval | activity level | activity type | venue type | ... | app type |
|---|---|---|---|---|---|
| 59 | 0 | [a1] | building | ... | — |
| 60 | 1.15 | [a1,a2,a1,a2] | route | ... | fitness |
| 61 | 1.99 | [a3,a2,a1] | park | ... | music |
| ... | ... | ... | ... | ... | ... |
| 288 | 0 | [a1] | building | ... | music |

Since these lifelogs are collected as data streams, and they have different granularities and semantics, processes in accordance with many embodiments of the invention synchronize the data streams by correlating them with a periodic time-interval. This periodic time-interval is referred to as an atomic-interval. Atomic-intervals are a 1×N matrix having N kind of lifelogs collected for a given time-interval. Each row in the table above shows an atomic-interval. The numbers in the first column indicate the order of the atomic-interval of the day. The sequentially collected lifelogs, such as activity type, are chronologically collected in an array. Average value, such as activity level, calculated based on pre-defined weights and their amount. Semantic data, such as activity type, venue, photo concept, or application category, are gathered by trustworthy APIs. The length of the atomic-interval can be decided by the designer depending on the precision requirement of the application, and thus there can exist the following separated atomic-intervals per day, assuming the unit of interval as minute.

$$\text{number\_of\_atomic\_intervals} = \frac{24 \text{ hours} \times 60 \text{ minutes}}{\text{time\_interval}} \quad (1)$$

In some embodiments, these atomic-intervals are organized as json format (as shown in FIG. 1), and then stored in a database on the user's device. The daily-activity-interval can be defined as a length of the daily activity. This daily-activity-interval can be determined by using an interval growing technique, described in greater detail below. This technique analyzes the characteristics of sequential atomic-intervals, and groups similar atomic-intervals together to make the daily-activity-interval.

Daily Activity Recognition

Daily activity segmentation is the process of partitioning a day into multiple sets of daily-activity-intervals. In a variety of embodiments, diverse data streams are pulled from a user's smartphone, synchronized by using atomic-intervals, and then segmented with an interval growing technique when chronological atomic-intervals have similar patterns of physical activity. For these reasons, determining a length of the atomic-interval must be the first step. Atomic-intervals of five minutes have been found to be effective, but one skilled in the art will recognize that many different atomic-intervals can be used without departing from the essence of the invention. Processes in accordance with numerous embodiments of the invention find situation transition moments by comparing the similarities of sequential five-minute atomic-intervals, and then use this amount of time as a base unit of daily activity segmentation. In the case of five-minute atomic-intervals, a day is divided into 288 atomic-intervals. Indications of changes of physical activity pattern can be involved in the changes of other attributes, which can be considered as ending one daily activity and starting another. For example, let's say a user has been working at the office, and he has been sitting on the chair. After 10 minutes, if he moves towards the cafeteria for lunch, this change of physical activity is recognized, and the moment is segmented. A daily-activity-interval is made by segmenting from the first atomic-interval to now. In other words, daily activity segmentation focuses on the interval-growing technique appropriate for daily activity segmentation in which the relevant atomic-intervals are identified by the patterns of physical activities.

In various embodiments, a binary interval growing (BIG) technique is used to determine whether consecutive atomic-intervals have similar patterns of physical activities. In order to compare the similarities, each atomic-interval is classified into the moving or the non-moving type of interval, and then the atomic-intervals are dealt with as one or the other. An example of how to segment atomic-intervals into daily-activity-intervals is described below.

```
Input: current atomic-interval I_i, seed atomic-interval S_j
Output: daily-activity-interval set R;
    1:  Set S_j = I_i if i = 0 and j = 0, or S_j = ∅, and then
        set k = 0;
    2:  repeat
    3:      Wait for next atomic-interval I_i = I_{i+1};
    4:      Extract activity level I_i and total amount of moving
            time t_i from I_i;
    5:      Extract activity level I_j and total amount of moving
            time t_j from S_j;
    6:      Calculate δ(i);
    7:      Make a daily-activity-interval r_k by segmenting from
            I_j to I_i, increment k and j, set new seed atomic-interval
            S_j = I_i if δ(i) = 1;
    8:  until the system is terminated.
    9:  return R
```

In this example, a seed atomic-interval $S_j$ is set up, and then $\delta(i)$ is continually calculated every five minutes to determine the similarity between sequential atomic-intervals. $\delta(i)$ can be represented by the following formula:

$$\delta(i) = \|f(S'_j) - f(I'_i)\|2/2 \quad (2)$$

where $S'_j$ is $\{l_j, t_j\}$, $I'_i$ is $\{l_i, t_i\}$, $f(x)$ is a classification algorithm to classify the non-moving (0) or the moving (1) type of atomic-interval, and $\delta(i)$ is a distance between $S_j$ and $I_i$. Thus, atomic-intervals can be segmented when $\delta(i)$ is equal to 1, and then a daily-activity-interval can be created by segmenting from $I_j$ to $I_i$. For example, if the type of the seed atomic interval is non-moving, then $f(S'_j)$ is equal to 0. After 5 minutes, if the type of the current atomic-interval is also non-moving, $f(I'_i)$ will be 0, and thus $\delta(i)$ is also equal to 0. However, after another 5 minutes, if the type of the current atomic-interval is moving, $f(I'_j)$ will be 1, and $\delta(i)=1$. Then, the moment is segmented, a daily-activity-interval is made by segmenting from $I_j$ to $I_i$, and the process is repeated again.

To recognize the daily activities, processes in accordance with many embodiments of the invention build a common daily activity model. Common multimedia event models can be built by identifying the global unique properties of each individual event. Event models can address several fundamental aspects of events, such as temporal, spatial, experiential, causal, structural, and informational aspects. In numerous embodiments, common event modeling captures physical (e.g, event occurrence time stamp and interval), logical (e.g, temporal domain), and/or relative (e.g, temporal relationships to other events) relationships between each aspect and an event. In a number of embodiments, these general aspects can be used as the categories of the modeling attributes, and the physical, logical, and relative components can be modified to match the daily activities.

In a variety of embodiments, common daily activity models can be built using Formal Concept Analysis (FCA) based on these general aspects of events. FCA is one powerful technique when data sources are limited, and even when they are uncertain, due to its specialty for discovering implicit information based on pre-defined binary relationships between object and attributes. FCA can be applied for daily activity recognition as follows. One daily activity D can be represented by a triplet T=(D, A, R), where A is a set of attributes, and R is the binary relationships between D and A, R⊆D×A. Once each daily activity is defined by the triplet, the triplet can then be converted into a cross table (e.g., Table). Then, all possible formal concepts $(X_i, Y_i)$, where $X_i \subseteq D_i$, and $Y_i \subseteq A_i$, are extracted from the cross table, and then are set up as nodes in the concept lattice, which is a graphical representation of the partially ordered knowledge. The hierarchy of formal concepts can be constructed by the following relations:

$$(X_1, Y_1) \leq (X_2, Y_2), \text{ if } X_1 \subseteq X_2 \leftrightarrow Y_1 \supseteq Y_2 \quad (3)$$

$X_i$ and $Y_i$ satisfy the following relations:

$$X'_i = \{a_i \in A_i | \forall d_i \in X_i, (d_i, a_i) \in R_i\} \quad (4)$$

$$Y'_i = \{d_i \in D_i | \forall a_i \in X_i, (d_i, a_i) \in R_i\} \quad (4)$$

|  |  | Attribute | | |
|---|---|---|---|---|
|  |  | Walking (Experiential) | Medium time-duration (Temporal) | Wok (Spatial) |
| Object | Working |  | X | X |
|  | Using Toilet | X |  | X |
|  | Commuting | X | X |  |

Figure 2:
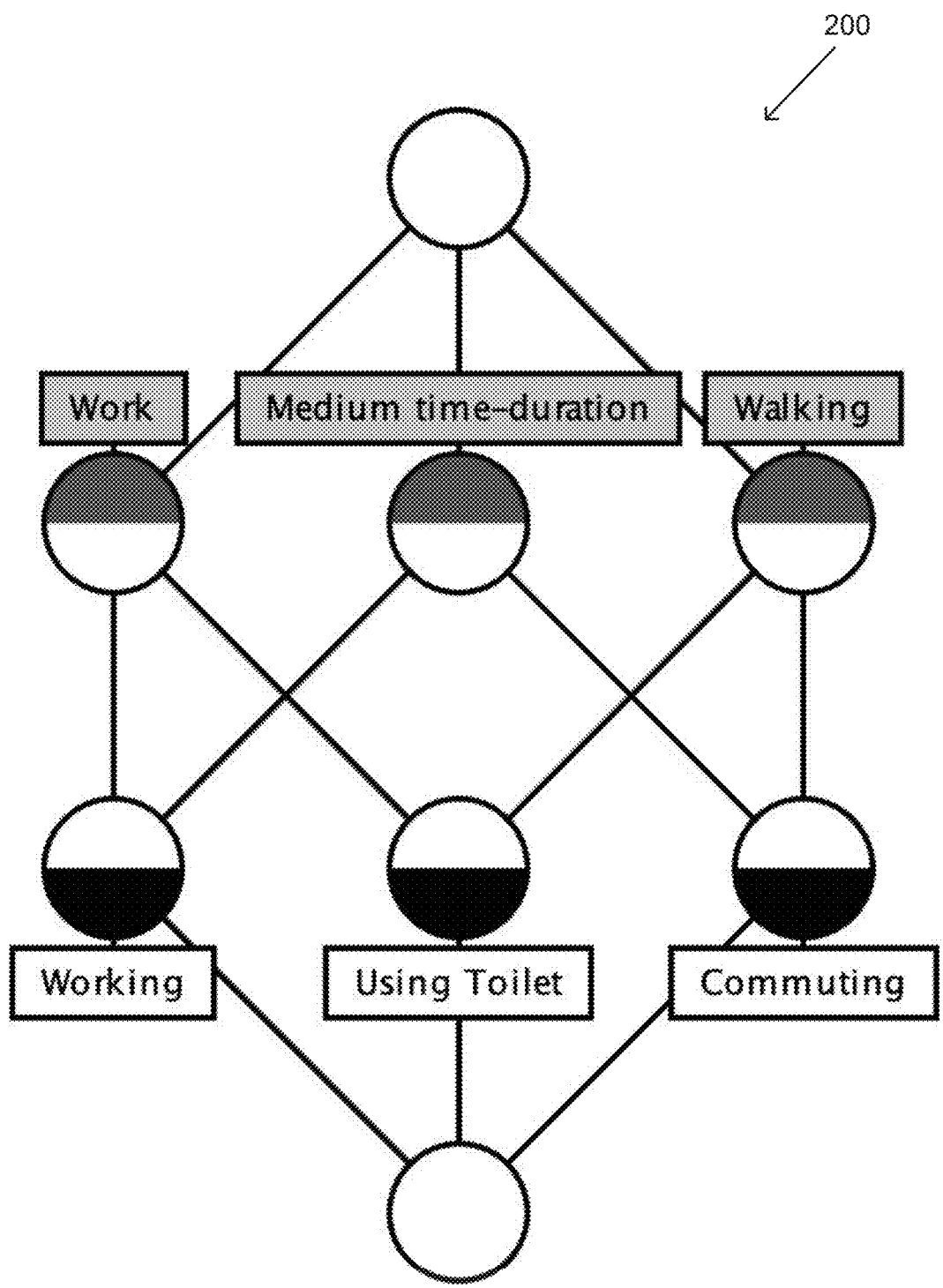
FIG. 2 illustrates a concept lattice in accordance with an embodiment of the invention.

The table above shows the simplified relationships between daily activity and their attributes. In order to build the FCA model, formal concepts can be derived from the cross table, such as (Working, {Medium time-duration, Work}), (Using Toilet, {Walking, Work}), (Commuting, {Walking. Medium time-duration}), ({Working. Using Toilet}, Work), ({Working, Commuting}, Medium time-duration), and ({Using Toilet, Commuting}, Walking). These formal concept pairs become each node in the concept lattice, and their hierarchy is determined by the formulas above. An example of a concept lattice in accordance with many embodiments of the invention is illustrated in FIG. 2. Concept lattice 200 reflects the partially ordered knowledge between each node. The top node and the bottom node indicate ({Working, Using Toilet, Commuting}, ∅), and (∅, {Walking, Medium time-duration, Work}), respectively. To navigate the concept lattice to obtain the expected results, depth first search is carried out with input attributes. For example, if input attributes are Medium time-duration and Work in FIG. 2, these two nodes will indicate one daily activity, Working.

FCA finds an expected result depending on the structural similarity between an input attribute set and pre-defined attribute sets. Thus, different kinds of input attributes can significantly affect the structural similarities. Because of this, it is necessary to estimate what attributes are important keys to separating each different daily activity, and find all unique daily activity structures composed of those attributes.

Moreover, an effective method is needed for estimating missing data while maintaining accuracy, considering that the daily activities are recognized in real-time on a user's device, and the device's status will not always be in the best condition. Lastly, given that the amount of actual user data is not always enough to train a powerful model, it would be beneficial to make a strong learner by using a group of weak learners.

An ensemble classifier that consists of many concept lattice bags, and its voting process to obtain a majority result from all the recognitions, can help to overcome these challenges. In certain embodiments, Bagging Formal Concept Analysis (BFCA), which applies the ensemble approach to FCA, is implemented in order to solve those challenges.

Figure 3:
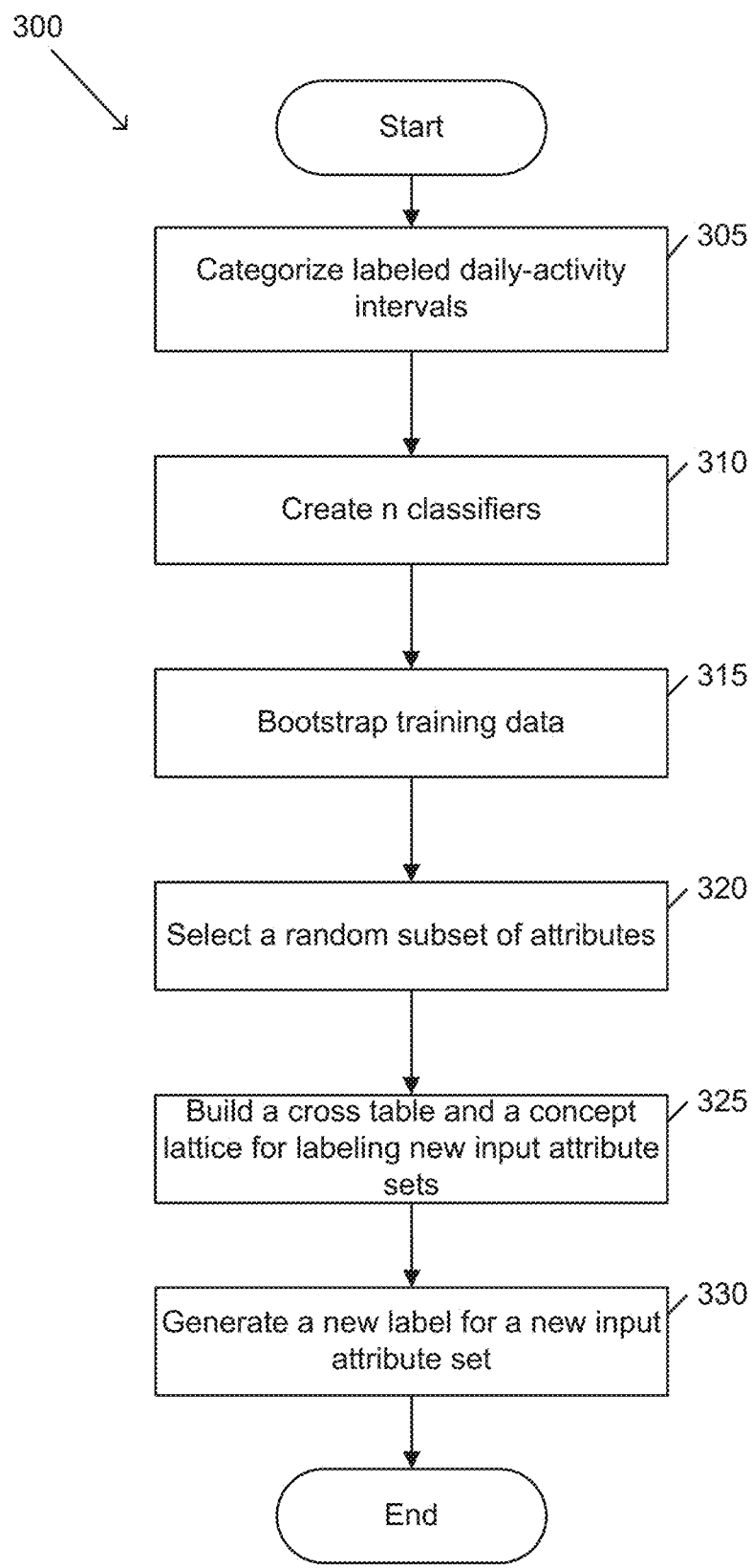
FIG. 3 illustrates a process for performing Bagging Formal Concept Analysis (BFCA) in accordance with an embodiment of the invention.

A process for performing Bagging Formal Concept Analysis (BFCA) in accordance with an embodiment of the invention is illustrated in FIG. 3. Process 300 categorizes (305) labeled daily-activity-intervals by each daily activity. Process 300 creates (310) n number of classifiers, where n is the number of the recognizable daily activities and m is the number of bags per classifier. Process 300 bootstraps (315) training data for each bag. In each bag, process 300 selects (320) a random subset of the attributes. In many embodiments, processes can select p/3 attributes, where p is the number of total attributes, and extract all unique relationships between the labeled daily activity and their randomly picked attributes.

Process 300 builds (325) a cross table in each bag by using those unique relationships, and a concept lattice. Concept lattices in accordance with certain embodiments of the invention only determine whether the given input attribute set can be the labeled daily activity. Process 300 then generates (335) a new label for an input attribute set. When an input attribute set is given (i.e., an unlabeled daily-activity-interval), concept lattices in accordance with a number of embodiments of the invention for each daily activity classifier can be navigated in order to calculate the possibility of being each daily activity and to choose the highest possibility among the results as a new label for the input attribute set.

Given that FCA requires discrete attributes, time-series values C, such as activity level, or time duration of daily-activity-intervals, can be converted into discrete space, such as w-dimensional space {high, medium, low}, by a vector $\overline{C} = \overline{c}_1, \overline{c}_2, \ldots, \overline{e}_i$. A discretization technique (such as, but not limited to, Symbolic Aggregate ApproXimation (SAX) can be used. SAX reduces a time series of arbitrary length n into the w-dimensional space by the following equation:

$$\overline{c}_i = \frac{w}{n} \sum_{j=\frac{n}{w}(i-1)+1}^{\frac{n}{w}i} c_j \quad (6)$$

In a number of embodiments, processes can create events with all facets (or attributes) by using all collectible data sources from multiple devices. An event can be considered as a single unit in itself, but it can form a personal chronicle once it is stored in the database. Thus, processes in accordance with certain embodiments of the invention store all the recognized daily activities in the database as events with as many data sources as possible, as illustrated in FIG. 1, and quantify the chronicle. This personal chronicle can then be used to model the person by using learning techniques and relating them to biomedical or behavioral signals.

In many embodiments, certain events require additional supplemental information, either to supplement a recognized activity and/or to more accurately recognize the activity itself. For example, processes in accordance with a number of embodiments of the invention collect supplemental information to record a food journal, either as a part of a personal chronicle or as a separate record. The foods and drinks we put in our bodies have a direct impact on our health and well-being. There have been numerous medical studies showing that unhealthy dietary habits can be a major cause of diseases such as obesity, kidney disorder, CVD, cancer, and diabetes. Clearly a well-balanced diet is very important to stay healthy. Food journaling has been demonstrated to encourage people to develop healthier dietary habits since it provokes self-reflection that can play a significant role in behavior change. Therefore, health care professionals and people who suffer from health-related disorders have tried to maintain a food journal so that they can analyze the health effects of their dietary intake. However, even though food journaling has been the main method of monitoring dietary intake for a long time, unobtrusive ways of keeping a food journal remain relatively undeveloped.

The traditional method of keeping a food journal is manually recording meals in as much detail as possible by including the portion size, number of servings and calories, time, location, or even the people around us. This detailed description is effective, but it is very easy to forget or procrastinate logging food entries, which then results in more difficulty recalling meals eaten or even early abandonment of the journaling process. Although remarkable technical progress in automating the food journaling process has been made, it is still highly dependent on the user to take initiative and then requires them to do things such as taking pictures of their food, scanning barcodes, or searching for foods in a food database. These methods tend to be unreliable and require many actions on the user's part which can then lead to the problems endemic, such as inaccurate or missed food entries and early abandonment.

There are currently two main challenges in improving food journaling: (1) triggering a food journaling process in a timely, proactive manner, and (2) improving the reactive self-reporting procedure while preserving high measuring accuracy. Processes in accordance with various embodiments of the invention offer an alternative method to current food journaling through an event-triggered Ecological Momentary Assessment (EMA). By considering both the proactive and reactive perspectives that can unobtrusively enhance the event-triggered EMA, processes in accordance with numerous embodiments of the invention can provide a novel and inventive solution to unobtrusive and effective food journaling.

To solve the first challenge in food journaling, a timely reminder is essential. The best time for food journaling is when people start eating a meal since they know what they are eating at that moment. Thus, processes in accordance with a number of embodiments of the invention begin with finding eating moments in order to trigger a food journaling process at the correct time. In numerous embodiments, two different kinds of eating moments are distinguished (e.g., one is "eating at a restaurant", and the other one is "eating at home"), with each eating moment being recognized based on different attributes. For example, an eating out moment can be recognized based on a location of the phone, time of day, and a user's historical records, while an eating in moment can be recognized based on a user's activity levels and heart rate signal.

In several embodiments, event-triggered EMA is implemented to maintain a food journal. To do this, systems in accordance with some embodiments of the invention provide an environment that allow a user to log their meals by describing what they just ate via voice commands. Essentially, taking pictures of foods and barcodes to create food entries have shown to be inaccurate or inconvenient. For this reason, processes in accordance with many embodiments of the invention use voice commands to create food entries by using speech-to-text technologies and natural language processing. Meanwhile, personal chronicle systems in accordance with numerous embodiments of the invention can automatically assesses the user's ecological moment by including the food entries as well as various contexts of the eating moment and thus unobtrusively complete the event-triggered EMA.

The goals of food journaling in accordance with a variety of embodiments of the invention include 1) providing an event-triggered EMA to automate the food journaling process, thereby 2) encouraging people to keep a well-balanced diet, as well as 3) helping them develop healthier dietary habits. A general eating moment model that can automatically and unobtrusively recognize the starting moment of eating, and then prompt the user to begin a voice command food journaling method can help to accomplish these goals. A sample use case of food journaling applications in accordance with various embodiments of the invention is as follows:

1. Users install an activity tracker application on a smartphone device and start using it with a wearable device (e.g., Charge 2, Blaze, Ionic, or Versa, which are currently the most common devices in the market).
2. After a cold start period lasting a week, the activity tracker system starts requesting a voice-command food journaling operation whenever it recognizes a starting moment of breakfast, lunch, or dinner. In some embodiments, activity tracker systems generate a unique pattern of vibration so that it can let the user know that it's time to make a food journal entry. Activity tracker systems in accordance with a number of embodiments of the invention provide other notifications (e.g., audio, verbal, screen, etc.) to signal that it's time to make a food journal entry.
3. Then, the user simply speaks whatever he is eating at that moment, such as "I'm eating a slice of pizza with buffalo wild wings and a cup of Coke for lunch".
4. After that, the activity tracker system extracts food items (e.g., pizza, buffalo wild wing, coke), quantity of the food (e.g., one slice, a cup), and meal type (e.g., lunch).
5. Finally, the activity tracker system makes an event-triggered EMA by capturing other contexts around the eating moment, such as glucose level, stress level, emotion, weather, location, other people with the user, or even past events before the eating activity.

Eating Moment Recognition

Processes in accordance with numerous embodiments of the invention trigger a food journaling process for two different kinds of eating moments. "eating at restaurant", or "eating at home". In numerous embodiments, recognizing an eating activity while outside of a person's home (e.g., restaurants) can be recognized based on the person's location and physical activity. However, it can be difficult to recognize when the user is eating at home, as it is challenging to find useful features that can distinguish an "eating event" from a "home event". In certain embodiments, recognizing eating moment can be performed by pulling a heart rate signal in the chronicle of daily activity in order to find the starting moment of the eating.

Heart rate is increased when people start eating a meal, and then maintain that increased rate while they are eating. This is supported by the studies published in psychophysiology, nutritional science, and electro-cardiology, which have proved that heart rate is generally higher after meals shows the sensor data processing pipeline starting with multi-modal sensor data tracking, such as heart rate and step count. The low-level signals are segmented whenever the pattern of physical activity is changed, and then extract features from the segmented results, and finally recognize eating moments through machine learning algorithms.

Segmentation can be defined as a process of partitioning a day into multiple sets of daily activity intervals. To segment a day, processes in accordance with various embodiments of the invention assume that transitions of physical activity pattern (e.g., moving to non-moving, or non-moving to moving) can be involved in the changes of other attributes, such as location, which can then be considered as ending one daily activity (e.g., "home event") and starting another (e.g., commuting). In certain embodiments, sequential atomic intervals of the day are segmented into moving (M) or non-moving (NM) type of daily activity intervals.

In some embodiments, sequential atomic intervals are segmented into coarse-grained daily activity intervals. Coarse-grained daily activity intervals in accordance with some embodiments of the invention are classified into daily activities, such a s "home e vent". The length of atomic interval in accordance with numerous embodiments of the invention are reduced from five-minutes to one-minute so that coarse-grained daily activity intervals can be re-segmented into fine-grained daily activity intervals, and thus allowing for the classification of an "eating at home" activity within the "home event". Such segmentations in accordance with many embodiments of the invention are performed using a recursive binary interval growing technique (RBIG), an example of which is described in the pseudocode below.

```
Input: current atomic interval A_i, a_i, seed atomic interval S_j, s_j
where a_i and s_j are 1 minute interval
Output: daily activity interval set R;
 1:  Set S_j = A_i if i = 0 and j = 0, or S_j = ∅, and then
     set k = 0, m = 0, p = 0;
 2:  Repeat
 3:    Wait for next atomic interval, A_i = A_{i+1}, i = i + 1;
 4:    Extract activity level I_i and total amount of moving
         time t_i from A_i;
 5:    Extract activity level I_j, and total amount of moving
         time t_j from S_j;
 6:    Calculate δ(i);
 7:    If δ(i) = 1, make a daily activity interval R_k by segmenting from
         A_j to A_i;
 8:    Set p = i, reset i = j, a_i = S_j, s_j = S_j;
 9:    Repeat in the daily activity-interval R_k
10:      Assign next atomic interval a_i = a_{i+1};
11:      Extract activity level I_i, and total amount of moving
           time t_i from a_i;
12:      Extract activity level I_j, and total amount of moving
           time t_j from s_j;
13:      Calculate δ(i);
14:      If δ(i) = 1, make a daily activity-interval r_m by segmenting
           from a_j to a_i;
15:      Set m = m + 1, j = i, set new seed atomic interval
           s_j = a_i
16:    until i = p
17:    Set k = K + 1, j = p set new seed atomic interval
```

-continued

```
    S_j = A_p
18: until the system is terminated.
19: return R, r
```

The pseudocode above shows the process of recursively re-segmenting a coarse-grained daily activity interval into fine-grained daily activity intervals. Processes in accordance with a variety of embodiments of the invention use five-minute segments for segmenting a coarse-grained daily activity interval. Once the coarse-grained daily activity interval is segmented, return to the seed atomic interval, and then re-segment the coarse-grained daily activity interval into fine-grained daily activity intervals by using one-minute atomic intervals. The seed atomic interval S is assigned at the beginning of the process, and the similarity $\delta(i)$ between the seed atomic interval S; and the incoming atomic intervals $A_i$ is calculated every interval minutes (e.g., 5 min, 1 min). $\delta(i)$ can be formulated as follows:

$$\delta(i) = \|f(S'_j) - f(I'_i)\|2/2 \qquad (7)$$

where $S'_j$ is $\{l_j, t_j\}$, $I'_i$ is $\{l_i, t_i\}$, $f(x)$ is a classifier to identify if an atomic interval is the moving (1) or non-moving (0) type of interval. When $\delta(i)$ is equal to 1, the atomic intervals are segmented from $I_j$ to $I_i$ and then designated as a coarse-grained daily activity interval $R_k$. After that, $R_k$ is segmented into fine-grained daily activity intervals $r_m$ by repeating the same process with one-minute atomic interval.

In numerous embodiments, processes can extract and select eating moment features from the fine-grained daily activity interval. Processes in accordance with some embodiments of the invention analyze historical activity data to identify latent features underlying the visible sensor data streams. For example, an analysis of historical activity data can identify that heart rate is increased when people start eating, as seen in $NM_2$ between time $t_1$ and $t_2$, and then the increased heart rate remained high during the meal time. In a number of embodiments, differences in an average heart rate between the eating moment and the past are used to identify eating moments since it can be another unique feature that determines the starting moment of eating. In some embodiments, all of the moving type of daily activity intervals can be excluded, which can highly affect the increase of heart rate, in order to correctly compare the difference in average heart rate. Such heart rate effects of dietary intake can be seen in between $NM_2$ and $NM_1$. In many embodiments, eating moment features can include (but are not limited to) average heart rate, heart rate variation, and heart rate difference between current and past daily activity intervals. Processes in accordance with a number of embodiments of the invention can extract additional features from activity patterns prior to an eating to be used in recognizing an eating moment, such as (but not limited to) step count and the amount of moving and non-moving time. For example, there will often be a certain amount of moving time just before beginning an eating activity due to events like preparing the food, or moving to the dining room.

In several embodiments, Correlation-based Feature Selection (CFS) criteria can be used to select the best subset of extracted features. This algorithm evaluates how accurately all the features in the feature subset are indicative of the target class. It also can evaluate which features are not correlated with each other by providing complementary information for each of them. To evaluate heuristically extracted features, the eating moment classifier can be trained with all the features, and then compared the recognition performance (F-measure) to those of other classifiers, which are trained without a particular feature subset. In various experiments, all of the extracted features show some performance degradation, which means these features are all highly indicative of the starting moment of eating activity. Based on this result, processes in accordance with several embodiments of the invention employ all the extracted features.

In a number of embodiments, processes can build a general eating moment model that can classify the fine-grained daily activity intervals into eating or non-eating moments. Building a general eating moment model in accordance with several embodiments of the invention can use relative values due to the fact that everyone has varying heart rate ranges. In a variety of embodiments, the heart rate C of each individual data is converted into heart rate levels, which are discretized w-dimensional space, by a vector $\overline{C} = \overline{c}_1, \overline{c}_2, \ldots, \overline{c}_i$. To do this, processes in accordance with some embodiments of the invention employ a discretization technique (such as, but not limited to, Symbolic Aggregate Approximation (SAX)). SAX reduces the time series of arbitrary length n into the w-dimensional space as follows:

$$\overline{c}_i = \frac{w}{n} \sum_{j=\frac{n}{w}(i-1)+1}^{\frac{n}{w}i} c_j \qquad (8)$$

Activity and time features (e.g., moving pattern, step count, and the amount of moving and non-moving time) in accordance with several embodiments of the invention are converted into discretized levels given that these also differ from person to person. In some embodiments, day-night differences in body temperature and heart rate are also accounted for by training breakfast, lunch, and/or dinner models separately. In some embodiments, a Support Vector Machine (SVM) with a Radial Basis Function kernel (RBF) is applied to the training dataset to train the classifier.

Voice Command Food Journaling

Activity tracking applications in accordance with several embodiments of the invention provide for voice command food journaling to allow a user to add food journal entries through a set of voice commands. In numerous embodiments, systems provide a voice command food journaling engine and define a basic sentence protocol that has to be spoken by a user to apply to text analysis. Solutions in accordance with a number of embodiments of the invention accept a voice based input describing food intake, transcribe the input to text, break down the input sentences according to the predefined protocol, and extract information for keeping a food journal. In some embodiments, activity tracking applications employ one or more APIs to capture, transcribe, and/or interpret captured voice commands.

The major components that are important on a food journal is food item, meal type and quantity. This information enables the ability to obtain nutrition information and calorie intake by querying a food database, such as USDA Food Composition Databases. In certain embodiments, activity tracking applications suggest that users include the aforementioned information with an actuating verb, such as "eat" or "have", when they describe what they am eating. The actuating verb could help to increase the accuracy of voice command analysis since it points out the most important sentences of all conversation. The quantity, food item, and meal type information should be listed sequentially after this actuating verb. Here are some examples of voice commands:

Protocol 1: I'm eating (actuating verb)/a (quantity)/cheeseburger (food item)/for lunch (meal type)
Protocol 2: Two (quantity)/garlic naans (first food item)/and a cup of (quantity)/Coke (second food item)

The first example shows a complete protocol that can be applied to the voice command. It has an actuating verb "eat", and then food item "cheeseburger", quantity "one" and meal type "lunch". In addition to the complete form, a simplified protocol can also be accepted, as can be seen in the second example. In certain embodiments, activity tracking applications can try to obtain food items (e.g., "garlic naan". "Coke"), and quantities of the foods (e.g., "two", "a cup"). Multiple food information also can be acceptable once it is listed sequentially.

After the speech has been converted to text (e.g., via Google Voice API), the next task is to extract the key information out of the text. Activity tracking applications in accordance with many embodiments of the invention extract the keywords in a sentence and the classification results of those keywords (e.g., utilizing a natural language processing APL such as (but not limited to) TextRazor). Sentences can be identified, which include actuating verbs, such as "eat", or "have". Keywords from the sentences can be filtered out by checking for foods, meal types and numbers, keeping only the necessary information to create a food entry. After that, the nearest numbers from the food items are extracted to map the quantity to the food. Lastly, if there is no meal type in the sentence, this information can be extracted from the tense of the verb or current time that the food entry was created.

Event-Triggered EMA

Personal ecological moments can be automatically assess without any questionnaires since activity tracking systems in accordance with several embodiments of the invention continuously monitor the chronicle of daily events, as well as semantic contexts and physiological signals. Therefore, once the activity tracking system recognizes an eating moment, processes in accordance with a number of embodiments of the invention can create an EMA of the eating activity consisting of stress level, glucose level, emotion, weather, location, other people with the user, and even past events before eating and their frequency. Additionally, if the user reacts to the voice command request, the journal entry can also include the food eaten, the quantity of the foods, the nutrition value, and the calorie intake in the event-triggered EMA. The ultimate goal of an event triggered EMA is to fully automate the food entry process, and thus keep a food journal without any user interventions, such as taking pictures.

Activity Tracking System

Figure 4:
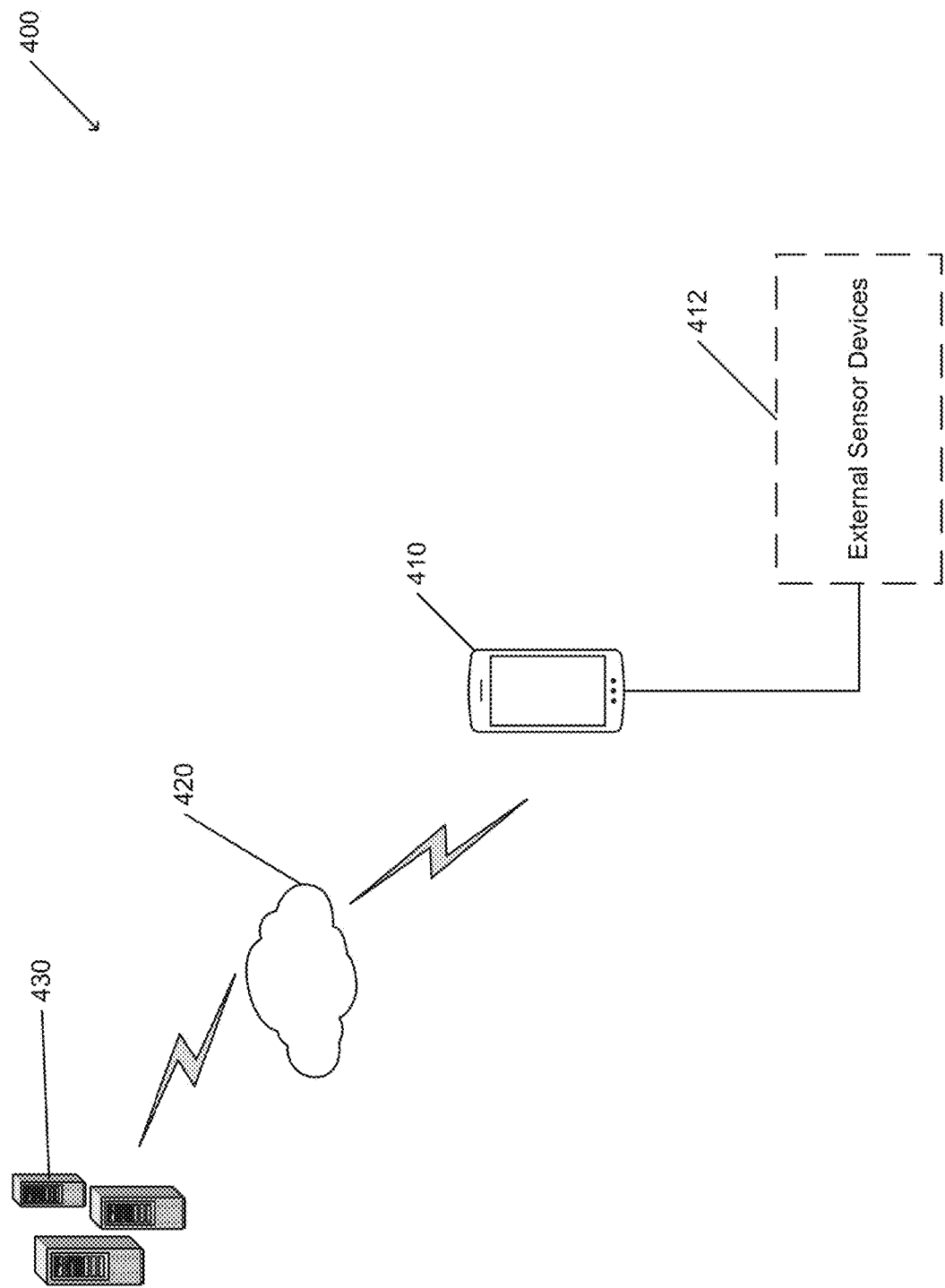
FIG. 4 is a conceptual illustration of an automatic activity tracking system in accordance with an embodiment of the invention.

Activity tracking systems in accordance with embodiments of the invention can capture a variety of data regarding a persons daily activities and automatically characterize those activities. A conceptual diagram of an activity tracking system in accordance with an embodiment of the invention is shown in FIG. 4. The activity tracking system 400 includes an activity tracking device 410 that can optionally communicate with one or more external sensor devices 412 and/or an external server system 430 as appropriate to the requirements of specific applications of embodiments of the invention. In a variety of embodiments, the activity tracking device 410 communicates with the remote server system 430 via a network 420. In a variety of embodiments, the network 420 is the Internet. In many embodiments, the network 420 is any wired or wireless network, such as a cellular network, between the activity tracking device 410 and the remote server system 430. In a number of embodiments, the remote server system 430 implemented using a single server system. In several embodiments, the remote server system 430 is implemented using multiple server systems.

Activity tracking devices can include any of a variety of sensors and/or devices, such as those described below and any other sensor as applicable to the specific requirements of applications of embodiments of the invention, to obtain data regarding the activity of the activity tracking device 410 and/or the user of the device. Sensors in accordance with many embodiments of the invention can include (but are not limited to) cameras, microphones, accelerometers, gyroscopes, heartrate trackers, location trackers, and microphones. In a variety of embodiments, activity tracking devices and/or remote server systems can provide a user interface allowing for visualizing and interacting with the data transmitted and/or received between the systems. In several embodiments, activity tracking devices and/or remote server systems provide an interface, such as an application programming interface (API) or web service, that provides some or all of the data to third-party systems for further processing. Access to the interface can be open and/or secured using any of a variety of techniques, such as by using client authorization keys, as appropriate to the requirements of specific applications of the invention.

Although a specific architecture of an activity tracking system in accordance with embodiments of the invention is discussed above and illustrated in FIG. 4, a variety of architectures, including sensors and other devices and techniques not specifically described above, can be utilized in accordance with embodiments of the invention. Furthermore, the processes described herein can be performed using any combination the activity tracking device and/or the remote server systems as appropriate to the requirements of specific applications of embodiments of the invention. For example, in some embodiments, application tracking applications operate on a set of cloud servers, receiving sensor information from a user's devices, where operations of the activity tracking system are distributed over multiple different devices within the system.

Activity Tracking Device

Figure 5:
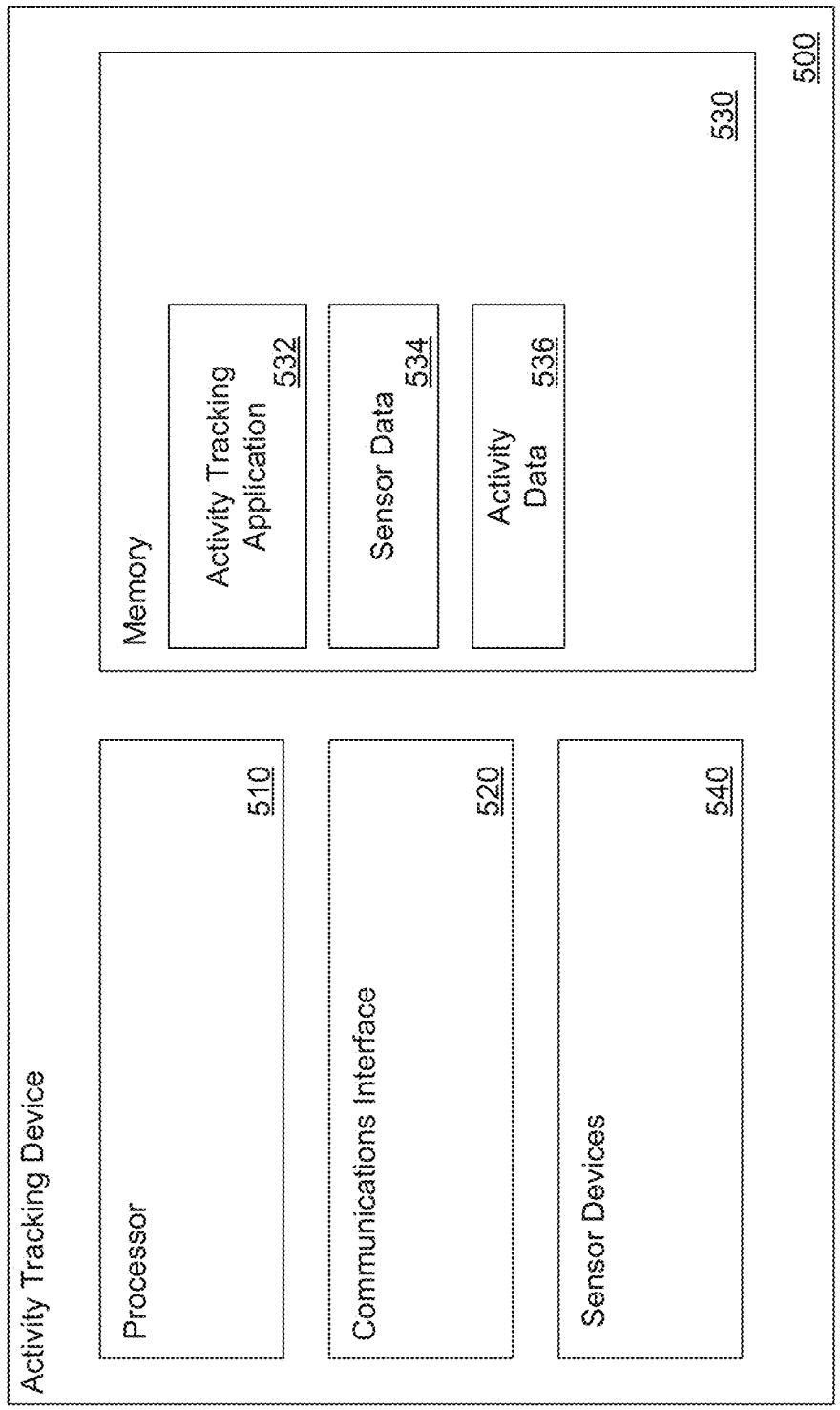
FIG. 5 is a conceptual illustration of an automatic activity tracking device in accordance with an embodiment of the invention.

Activity tracking devices in accordance with embodiments of the invention can capture and/or characterize a variety of activity data. A conceptual illustration of an activity tracking device in accordance with an embodiment of the invention is shown in FIG. 5. The activity tracking device 500 includes a processor 510 in communication with memory 530. The activity tracking device 500 can also include one or more communication interfaces 520 capable of sending and receiving data. In a number of embodiments, the communication interface 520 is in communication with the processor 510, the memory 530, and/or the sensor device(s) 540. In several embodiments, the memory 530 is any form of storage storing a variety of data, including, but not limited to, an activity tracking application 532, sensor data 534, and activity data 536. In many embodiments, the activity tracking application 532, sensor data 534, and/or activity data 536 are stored using an external server system and received by the activity tracking device 500 using the communications interface 520. The communications interface 520 can allow communication via any of a variety of wired and/or wireless communication systems, including any of a variety of RF communication systems such as Bluetooth, 802.11 wireless networks, and cellular networks.

Sensor devices can include accelerometers, location tracking sensors, pressure transducers, heartbeat sensors, step trackers, moisture sensors, and any other device capable of measuring data regarding the activity of the activity tracking device and/or its user as appropriate to the requirements of specific applications of embodiments of the invention. In many embodiments, sensors can include a Global Positioning System (GPS) receiver in order to determine the location, speed, and/or acceleration of the activity tracking device. However, it should be noted that any location-determining techniques, such as cellular tower triangulation, wireless network geolocation techniques, and dead reckoning techniques, could be utilized as appropriate to the requirements of specific applications of embodiments of the invention. Sensor devices can be included within a primary activity tracking device and/or located external to the activity tracking device. In some embodiments, sensor devices are located on a separate wearable device that communicates sensor data to the primary activity tracking device. Activity tracking devices can communicate with external sensor devices using communications interfaces as appropriate to the requirements of specific applications of embodiments of the invention.

Processors can be directed by activity tracking applications to perform a variety of activity tracking processes, such as processing sensor data to generate activity data. A variety of activity tracking processes that can be performed in accordance with embodiments of the invention are described in more detail below.

Although specific architectures for activity tracking devices in accordance with embodiments of the invention are conceptually illustrated in FIG. 5, any of a variety of architectures, including those that store data or applications on disk or some other form of storage and are loaded into memory at runtime, can also be utilized. Additionally, any of the data utilized in the system can be cached and transmitted once a network connection (such as a wireless network connection via the communications interface) becomes available. In a variety of embodiments, a memory includes circuitry such as, but not limited to, memory cells constructed using transistors, that are configured to store instructions. Similarly, a processor can include logic gates formed from transistors (or any other device) that dynamically perform actions based on the instructions stored in the memory. In several embodiments, the instructions are embodied in a configuration of logic gates within the processor to implement and/or perform actions described by the instructions. In this way, the systems and methods described herein can be performed utilizing both general-purpose computing hardware and by single-purpose devices.

Activity Tracking Application

Figure 6:
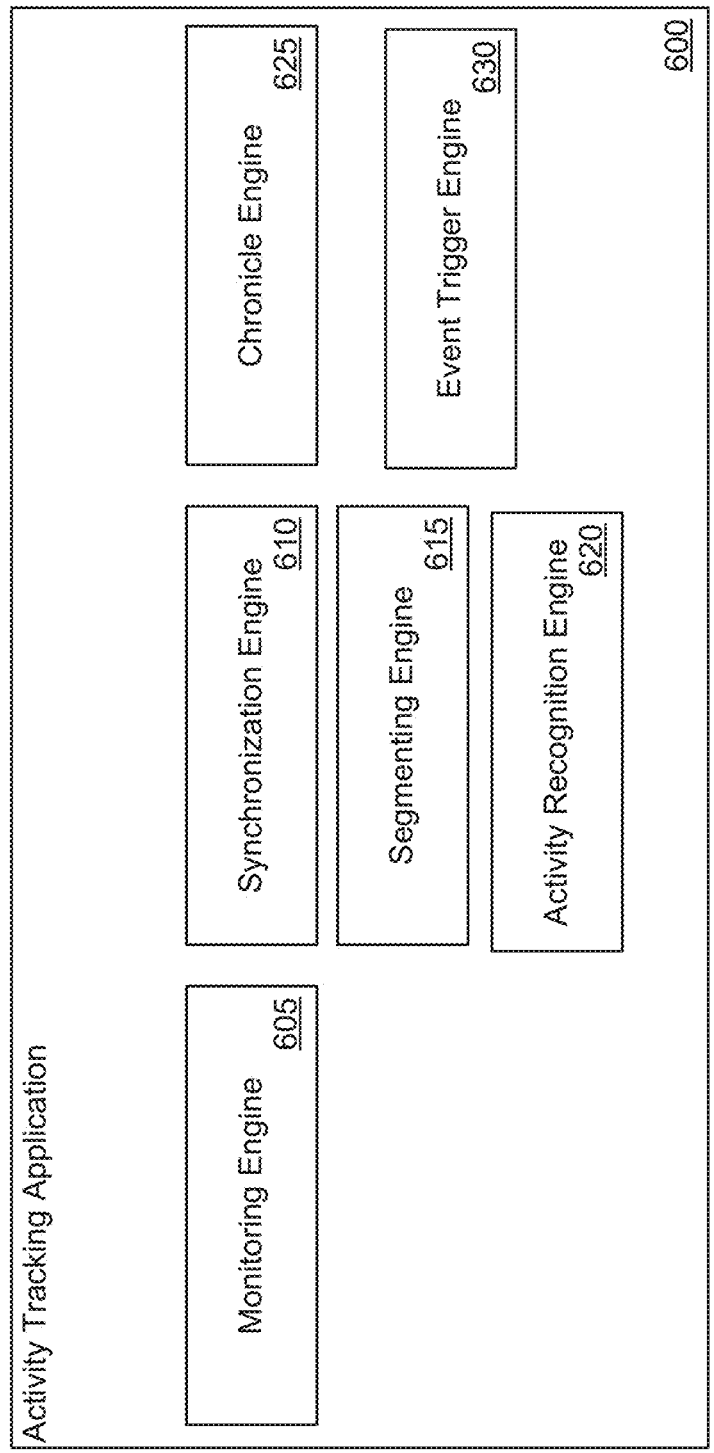
FIG. 6 is a conceptual illustration of an automatic activity tracking application in accordance with an embodiment of the invention.

An activity tracking application in accordance with an embodiment of the invention is illustrated in FIG. 6. Application 600 includes monitoring engine 605, synchronization engine 610, segmenting engine 615, activity recognition engine 620, activity recognition engine 620, chronicle engine 625, and event trigger engine 630.

In various embodiments, monitoring engines can monitor and receive multimodal inputs from a user's devices. Multimodal inputs in accordance with several embodiments of the invention include various data streams and/or logs with data over a given period of time. In some embodiments, multimodal inputs can be generated by various sources including (but not limited to) applications, sensors, and/or networked computers. In several embodiments, user devices can include one or more of a smartphone, a wearable smart device, networked servers, Internet of Things (IoT) devices, and/or personal computers.

Synchronization engines in accordance with several embodiments of the invention can take monitored multimodal inputs and synchronize them to a single timeline. In a number of embodiments, synchronization engines can divide the data from each of the multimodal inputs into atomic intervals. Atomic intervals in accordance with a variety of embodiments of the invention are the smallest time interval that is evaluated and labeled with activities.

In certain embodiments, segmenting engines can identify segments of atomic intervals that can be treated as a single daily activity. Segments in accordance with several embodiments of the invention include one or more atomic intervals and represent a single daily activity. In some embodiments, segmenting engines use a binary interval growing (BIG) procedure to group atomic intervals into segments. Transitions between segments in accordance with certain embodiments of the invention can be identified based on various transition criteria including (but not limited to) transitions from a motion state to a non-motion state, transitions from one location to another, transitions in a user's device state, and/or detection of a triggering event (such as, but not limited to, a user input, a notification, and/or a sudden change in the multimodal input).

Activity recognition engines in accordance with a variety of embodiments of the invention can recognize activities for each identified segment. In some embodiments, activity recognition is performed using a classification model, such as (but not limited to) Bagging Formal Concept Analysis (BFCA), FCA, SVMs, and/or random classifiers. Activity recognition engines in accordance with some embodiments of the invention can label each segment with associated activities.

In several embodiments, chronicle engines can generate and store activity data for an individual in a personal chronicle. Personal chronicles in accordance with certain embodiments of the invention can be used for modeling a user's activities, which can then be applied to various applications in productivity and health.

Event trigger engines in accordance with some embodiments of the invention can be used to retrieve supplemental data upon the detection of an event. Events in accordance with some embodiments of the invention can include (but are not limited to) detecting that a segment cannot be labeled, determining that a particular activity has been recognized (e.g., an eating moment), and/or at a certain time each day. Upon detection of the event, event trigger engines in accordance with various embodiments of the invention can trigger a trigger event to retrieve supplemental data. In numerous embodiments, trigger events can include (but are not limited to) providing a prompt for journaling (or labeling), providing notifications, and/or retrieving supplemental information to be associated with a given segment.

Although a specific architecture of an activity tracking application in accordance with embodiments of the invention is discussed above and illustrated in FIG. 6, a variety of architectures, including sensors and other devices and techniques not specifically described above, can be utilized in accordance with embodiments of the invention. Furthermore, the processes described herein can be performed using any combination the activity tracking device and/or the remote server systems as appropriate to the requirements of specific applications of embodiments of the invention.

Methods for Activity Tracking

Figure 7:
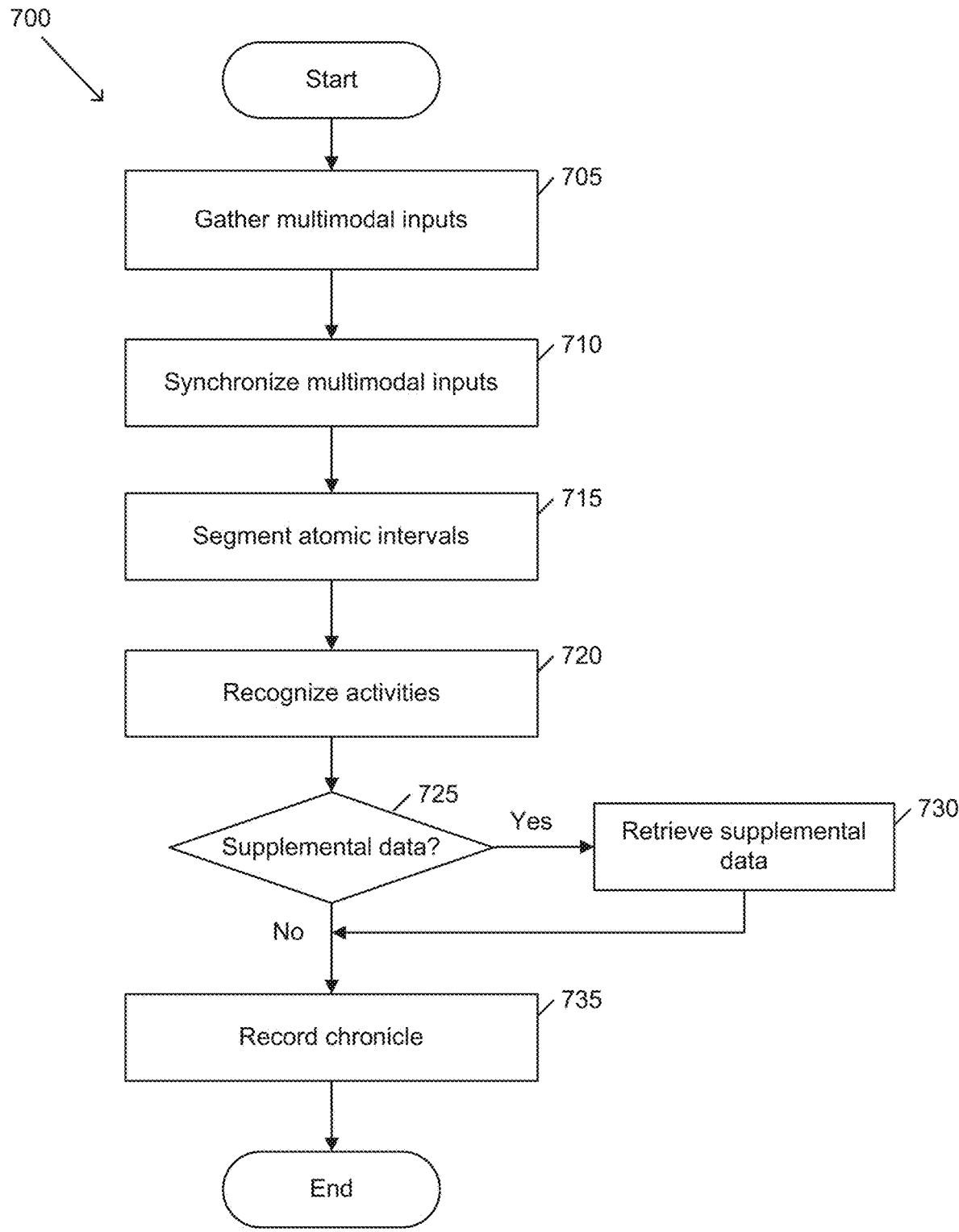
FIG. 7 conceptually illustrates a process for automatic activity tracking in accordance with an embodiment of the invention.

A process for activity tracking in accordance with an embodiment of the invention is illustrated in FIG. 7. Process 700 gathers (705) multimodal inputs from various sensors. Process 700 synchronizes (710) the multimodal inputs to identify correlations between the multimodal inputs. Process 700 segments (715) atomic intervals into larger daily activity intervals. Process 700 recognizes (720) activities for the segmented intervals. Process 700 determines (725) whether to retrieve supplemental data. Processes in accordance with some embodiments of the invention can determine that supplemental data is needed based on a variety of factors, including (but not limited to) whether an activity is recognized, based on a type of recognized activity, etc. When process 700 determines supplemental data is desired, the process retrieves (730) supplemental data. Supplemental data can include (but is not limited to) data for labeling an activity, providing additional information for a recognized activity, and/or recording environmental data related to a recognized activity. In some embodiments, supplemental data can be retrieved in a variety of ways, including (but not limited to) as voice commands or other inputs from a user, from a cloud service, and/or from a user's device(s). When process 700 determines that supplemental data is not required, or after retrieving supplemental data, process 700 records (735) the identified activities and intervals as a part of a personal chronicle. Personal chronicles (or food journals) in accordance with a variety of embodiments of the invention can include various data structures that reflect events and/or activities associated with a user.

Although a specific process for activity tracking in accordance with embodiments of the invention is discussed above and illustrated in FIG. 7, a variety of processes, can be utilized in accordance with embodiments of the invention. Furthermore, the processes described herein can be performed using any combination user device(s) and/or server systems as appropriate to the requirements of specific applications of embodiments of the invention.

Although the present invention has been described in certain specific aspects, many additional modifications and variations would be apparent to those skilled in the art. It is therefore to be understood that the present invention may be practiced otherwise than specifically described. Thus, embodiments of the present invention should be considered in all respects as illustrative and not restrictive.

What is claimed is:

1. A method for tracking activities from a plurality of multimodal inputs, wherein the method comprises:
   receiving a plurality of multimodal inputs from devices associated with a user, wherein the plurality of multimodal inputs is based on activities of the user;
   synchronizing the plurality of multimodal inputs;
   generating segments from the synchronized multimodal inputs;
   recognizing an activity associated with each generated segment using a model based on a plurality of classifiers each corresponding to a different activity type, wherein a random subset of attributes is selected for each classifier of the plurality of classifiers, and the plurality of classifiers is trained based on the associated selected random subsets of attributes, and wherein attributes in the selected random subsets of attributes are related to aspects of activities including the recognized activity; and
   recording the recognized activities in a storage.

2. The method of claim 1, wherein recognizing the activity comprises:
   training the plurality of classifiers based on the associated selected random subsets of attributes;
   generating the model for labeling new input attribute sets based on the trained plurality of classifiers; and
   generating a label for a new attribute set using the generated model.

3. The method of claim 2, wherein the generated new model comprises at least one of a cross table and a concept lattice.

4. The method of claim 1, wherein the plurality of multimodal inputs comprises at least one of data from applications operating on a mobile phone and data from a set of one or more sensors.

5. The method of claim 1, wherein synchronizing the plurality of multimodal inputs comprises associating data from the multimodal inputs from a given time period with a plurality of atomic intervals, wherein each atomic interval has a same duration.

6. The method of claim 1, wherein generating segments from the synchronized multimodal inputs comprises performing a binary interval growing operation.

7. The method of claim 6, wherein performing a binary interval growing operation comprises:
   identifying an initial atomic interval for a particular segment;
   for a second atomic interval, identify a transition moment; and
   identifying each atomic interval from the initial atomic interval to the second atomic interval as a single segment.

8. The method of claim 7, wherein the transition moment comprises a change between a non-moving state and a moving state.

9. The method of claim 1, further comprising:
   determining whether to retrieve supplemental data upon detecting a trigger event; and
   upon determining that the trigger event has been detected, retrieving the supplemental data.

10. The method of claim 9, wherein the trigger event is recognition of an eating moment and retrieving the supplemental data comprises providing an audio prompt to record a food journal entry.

11. An activity tracking device for tracking activities from a plurality of multimodal inputs, wherein the activity tracking device comprises:
   a set of one or more processors; and
   a non-volatile storage containing an activity tracking application for causing the set of processors to perform the steps of:
      receiving a plurality of multimodal inputs from devices associated with a user, wherein the plurality of multimodal inputs is based on activities of the user;
      synchronizing the plurality of multimodal inputs;
      generating segments from the synchronized multimodal inputs;
      recognizing an activity associated with each generated segment using a model based on a plurality of classifiers each corresponding to a different activity type, wherein a random subset of attributes is selected for each classifier of the plurality of classifiers, and the plurality of classifiers is trained based on the associated selected random subsets of attributes, and wherein attributes in the selected random subsets of attributes are related to aspects of activities including the recognized activity; and recording the recognized activities in a storage.

12. The activity tracking device of claim 11, wherein recognizing the activity comprises:
    training the plurality of classifiers based on the associated selected random subsets of attributes;
    generating the model for labeling new input attribute sets based on the trained plurality of classifiers; and
    generating a label for a new attribute set using the generated model.

13. The activity tracking device of claim 12, wherein the generated new model comprises at least one of a cross table and a concept lattice.

14. The activity tracking device of claim 11, wherein the plurality of multimodal inputs comprises at least one of data from applications operating on a mobile phone and data from a set of one or more sensors.

15. The activity tracking device of claim 11, wherein synchronizing the plurality of multimodal inputs comprises associating data from the multimodal inputs from a given time period with a plurality of atomic intervals, wherein each atomic interval has a same duration.

16. The activity tracking device of claim 11, wherein generating segments from the synchronized multimodal inputs comprises performing a binary interval growing operation.

17. The activity tracking device of claim 16, wherein performing a binary interval growing operation comprises:
    identifying an initial atomic interval for a particular segment;
    for a second atomic interval, identify a transition moment; and
    identifying each atomic interval from the initial atomic interval to the second atomic interval as a single segment.

18. The activity tracking device of claim 17, wherein the transition moment comprises a change between a non-moving state and a moving state.

19. The activity tracking device of claim 11, further comprising:
    determining whether to retrieve supplemental data upon detecting a trigger event; and
    upon determining that the trigger event has been detected, retrieving the supplemental data.

20. The activity tracking device of claim 19, wherein the trigger event is recognition of an eating moment and retrieving the supplemental data comprises providing an audio prompt to record a food journal entry.

* * * * *